US012411064B2

(12) United States Patent
Li et al.

(10) Patent No.: US 12,411,064 B2
(45) Date of Patent: *Sep. 9, 2025

(54) METHODS FOR HEAT-ASSISTED ENZYME DIGESTION

(71) Applicant: Waters Technologies Corporation, Milford, MA (US)

(72) Inventors: Wenjing Li, Shrewsbury, MA (US); Beatrice Muriithi, Attleboro, MA (US); Anna Boardman, Watertown, MA (US); Matthew A. Lauber, North Smithfield, RI (US)

(73) Assignee: Waters Technologies Corporation, Milford, MA (US)

( * ) Notice: Subject to any disclaimer, the term of this patent is extended or adjusted under 35 U.S.C. 154(b) by 914 days.

This patent is subject to a terminal disclaimer.

(21) Appl. No.: 17/466,389

(22) Filed: Sep. 3, 2021

(65) Prior Publication Data

US 2021/0396632 A1    Dec. 23, 2021

Related U.S. Application Data

(63) Continuation-in-part of application No. 17/314,541, filed on May 7, 2021, now Pat. No. 12,202,857.
(Continued)

(51) Int. Cl.
*G01N 1/40*    (2006.01)
*C12M 1/40*    (2006.01)
(Continued)

(52) U.S. Cl.
CPC ........... *G01N 1/4044* (2013.01); *C12M 21/18* (2013.01); *G01N 1/2813* (2013.01); *G01N 1/312* (2013.01); *G01N 2001/282* (2013.01)

(58) Field of Classification Search
CPC .... G01N 1/4044; G01N 1/2813; G01N 1/312; G01N 2001/282; C12M 21/18
See application file for complete search history.

(56) References Cited

U.S. PATENT DOCUMENTS 8,143,071 B2    3/2012   Gjerde
8,268,247 B2    9/2012   Guzman
(Continued)

FOREIGN PATENT DOCUMENTS

EP    1521637 B1    10/2011
EP    2753634 B1    11/2017
(Continued)

OTHER PUBLICATIONS

Yoshizawa, Shunsuke, Tsutomu Arakawa, and Kentaro Shiraki. "Thermal aggregation of human immunoglobulin G in arginine solutions: contrasting effects of stabilizers and destabilizers." International journal of biological macromolecules 104 (2017): 650-655. (Year: 2017).*
(Continued)

*Primary Examiner* — Louise W Humphrey
*Assistant Examiner* — Candice Lee Swift
(74) *Attorney, Agent, or Firm* — Womble Bond Dickinson-US LLP

(57) ABSTRACT

The present disclosure relates to a kit for sample preparation, the kit including a solid support surface with a polymer coating covering the solid support surface, wherein the
(Continued)

polymer coating reduces undesired interactions between the sample and the solid support surface, a buffer comprising arginine and methionine, and a vessel for containing the solid support surface and the buffer.

5 Claims, 24 Drawing Sheets

Related U.S. Application Data

(60) Provisional application No. 63/022,056, filed on May 8, 2020.

(51) Int. Cl.
*G01N 1/28* (2006.01)
*G01N 1/31* (2006.01)

(56) References Cited

U.S. PATENT DOCUMENTS

| | | |
|---|---|---|
| 9,114,383 B2 | 8/2015 | Gjerde et al. |
| 10,092,894 B2 | 10/2018 | Brousmiche et al. |
| 10,266,819 B2 | 4/2019 | Meyer et al. |
| 11,020,737 B2 | 6/2021 | Cowieson et al. |
| 11,103,831 B2 | 8/2021 | Jokhadze et al. |
| 11,180,533 B2 | 11/2021 | Pullagurla et al. |
| 11,246,922 B1 | 2/2022 | Cruz Rodriguez |
| 11,312,744 B2 | 4/2022 | Yin et al. |
| 11,346,742 B2 | 5/2022 | Vogt et al. |
| 2005/0277155 A1 | 12/2005 | Vinet et al. |
| 2015/0361415 A1 | 12/2015 | Meyer et al. |
| 2016/0341640 A1 | 11/2016 | Brevnov et al. |
| 2016/0341704 A1 | 11/2016 | Meyer et al. |
| 2017/0315132 A1 | 11/2017 | Kaur et al. |
| 2019/0086371 A1 | 3/2019 | Lauber et al. |
| 2019/0317059 A1 | 10/2019 | Zhang et al. |
| 2019/0366236 A1 | 12/2019 | Walch et al. |
| 2020/0094165 A1 | 3/2020 | Nelson et al. |
| 2020/0110094 A1 | 4/2020 | Mao et al. |
| 2020/0326315 A1 | 10/2020 | Tian et al. |
| 2021/0396632 A1 | 12/2021 | Li et al. |
| 2022/0204953 A1 | 6/2022 | Liu et al. |
| 2022/0242906 A1 | 8/2022 | Ng et al. |

FOREIGN PATENT DOCUMENTS

| | | |
|---|---|---|
| EP | 2329257 B1 | 3/2018 |
| EP | 2951300 B1 | 3/2020 |
| WO | 2005113129 A1 | 12/2005 |
| WO | 2006021217 A1 | 3/2006 |
| WO | 2006063625 A1 | 6/2006 |
| WO | 2006068619 A1 | 6/2006 |
| WO | 2013162951 A1 | 10/2013 |
| WO | 2014120890 A1 | 8/2014 |
| WO | 2015059478 A1 | 4/2015 |
| WO | 2018005445 A9 | 2/2019 |
| WO | 2019028187 A1 | 2/2019 |
| WO | 2020168156 A1 | 8/2020 |
| WO | 2020180645 A1 | 9/2020 |
| WO | 2020186135 A1 | 9/2020 |
| WO | 2020214675 A1 | 10/2020 |
| WO | 2021046110 A1 | 3/2021 |
| WO | 2022078524 A2 | 4/2022 |

OTHER PUBLICATIONS

Kim, Nam Ah, et al. "Arginine as a protein stabilizer and destabilizer in liquid formulations." International Journal of Pharmaceutics 513.1-2 (2016): 26-37. (Year: 2016).*
Lam et al. Journal of Pharmaceutical Sciences, vol. 86, No. 11, Nov. 1997 (Year: 1997).*
Shiraki, Kentaro, et al. "Biophysical effect of amino acids on the prevention of protein aggregation." The Journal of Biochemistry 132.4 (2002): 591-595. (Year: 2002).*
Levy-Sakin, Michal, et al. "The influence of chemical chaperones on enzymatic activity under thermal and chemical stresses: common features and variation among diverse chemical families." PLoS One 9.2 (2014): e88541. (Year: 2014).*
Krenkova, Jana, Nathan A. Lacher, and Frantisek Svec. "Highly efficient enzyme reactors containing trypsin and endoproteinase LysC immobilized on porous polymer monolith coupled to MS suitable for analysis of antibodies." Analytical chemistry 81.5 (2009): 2004-2012. (Year: 2009).*
Subramanian, Aravind, et al. "Comparison of techniques for enzyme immobilization on silicon supports." Enzyme and Microbial Technology 24. 1-2 (1999): 26-34. (Year: 1999).*
Plueddemann, Edwin P., and Edwin P. Plueddemann. "Aqueous Solutions of Silane Coupling Agents." Silane Coupling Agents (1982): 49-73. (Year: 1982).*
Liu, Ji, Shuke Wu, and Zhi Li. "Recent advances in enzymatic oxidation of alcohols." Current opinion in chemical biology 43 (2018): 77-86. (Year: 2018).*
Shiraki, Kentaro, Shunsuke Tomita, and Naoto Inoue. "Small amine molecules: solvent design toward facile improvement of protein stability against aggregation and inactivation." Current pharmaceutical biotechnology 17.2 (2016): 116-125. (Year: 2016).*
Chen et al. "Epoxy silanes in reactive polymer emulsions." J. Coatings Technol. 69.875(1997): 49-55.
Liu et al. "Recent advances in enzymatic oxidation of alcohols." Curr. Opin. Chem. Biol. 43(2018): 77-86.
Master Organic Chemistry; https://www.masterorganicchemistry.com/2017/09/01/reductive-amination/; accessed Mar. 22, 2024.
Nist; https://www.nist.gov/programs-projects/nist-monoclonmal-antibody-reference-material-8671; accessed Mar. 22, 2024.
Plueddemann et al. "Aqueous solutions of silane coupling agents." Silane Coup. Agents. (1991): 55-78.
Subramanian et al. "Comparison of techniques for enzyme immobilization on silicon supports." Enzy. Microbiol. Technol. 21.1-2(1999): 26-34.
Liang et al. "Hydrophilic monolith based immobilized enzyme reactors in capillary and on microchip for high-throughput proteomic analysis." J. Chromatrogr. A. 1218(2011): 2898-2905.
International Search Report and Written Opinion issued in International Application No. PCT/IB2021/053910 dated Jul. 22, 2021.
Naldi et al. "Immobilized enzyme-based analytical tools in the-omics era: Recent advances." J. Pharma. Biomed. Anal. 160(2018): 222-237.
Meller et al. "Preparation of an improved hydrophilic monolith to make trypsin immobilized microreactors." J. Chromatogr. B. 1043(2017): 128-137.
Ampon et al. "The effect of attachment of hydrophobic modifiers on the catalytic activities of lipase and trypsin." Biocatalysis Non-Conventional Media. 8(1992):331-338.
Cepham Life Sciences; https ://www.cephamls.com/edc-1-ethyl-3-3-di methylaminopropylcarbodiimide-hydrochloride/#:-:text=EDC% 20is %20a%20water%2 Dsoluble, and %20hapten %2 Dcarrier% 20protein %20conjugation.; accessed Oct. 31, 2023 (Year: 2019).
Fan et al. "Microchip bioreactors based on trypsin-immobilized graphene oxide-poly(urea-formaldehyde) composite coating for efficient peptide mapping." Talanta. 117(2013): 119-126.
Jun et al. "Trypsin Coatings on Electrospun and Alcohol-Dispersed Polymer Nanofibers for a Trypsin Digestion Column." Anal. Chem. 82(201): 7828-7834.
Krenkova et al. "Highly Efficient Enzyme Reactors Containing Trypsin and Endoproteinase LysC Immoblized on Porous Polymer Monolith Coupled to MS Suitable for Analysis of Antibodies." Anal. Chem. 81(2009): 2004-2012.
Nicoli et al. "Trypsin immoblization on three monolithic disks for on-line protein digestion." J. Pharm. Biomed. Anal. 48 (2008): 398-407.
Shi et al. "Hydrophilic polydopamine-coated magnetic graphene nanocomposites for highly efficient tryptic immobilization." Proteomics. 14(2014): 1457-1463.

(56) References Cited

OTHER PUBLICATIONS

Wang et al. "Combination of online enzyme digestion with stable isotope labeling for high-throughput quantitative proteome analysis." Proteomics. 12(2012): 3129-3137.

Wang et al. "Integration of immobilized trypsin bead beds for protein digestion within a microfluidic chip incorporating capillary electrophoresis separations and an electrospray mass spectrometry interface." Rapid Comm. Mass Spec. 12 (2012): 3129-3137.

"Polyethylene glycol." Retrieved Mar. 7, 2023. https://www.sciencedirect.com/topics/materials-science/polyethylene-glycol#:~:tex=1.1PEGchemistry.

Ashenhurst. Amines: Reductive Animation. Retrieved on Mar. 7, 2023. https://www.masterorganicchemistry.com/2017/09/01/reutive-animation/.

Brockman et al. "A Multistep Chemical Modification Procedure to Create DNA Arrays on Gold Surfaces for the Study of Protein-DNA Interactions with Surface Plasmon ResonanceImaging." J. Am. Chem. Soc. 121(1999): 8044-8051.

Dulay et al. "Enhanced Proteolytic Activity of Covalently Bound Enzymes in Photopoylmerized Sol Gel." Anal. Chem. 77(2005): 4604-4610.

\* cited by examiner

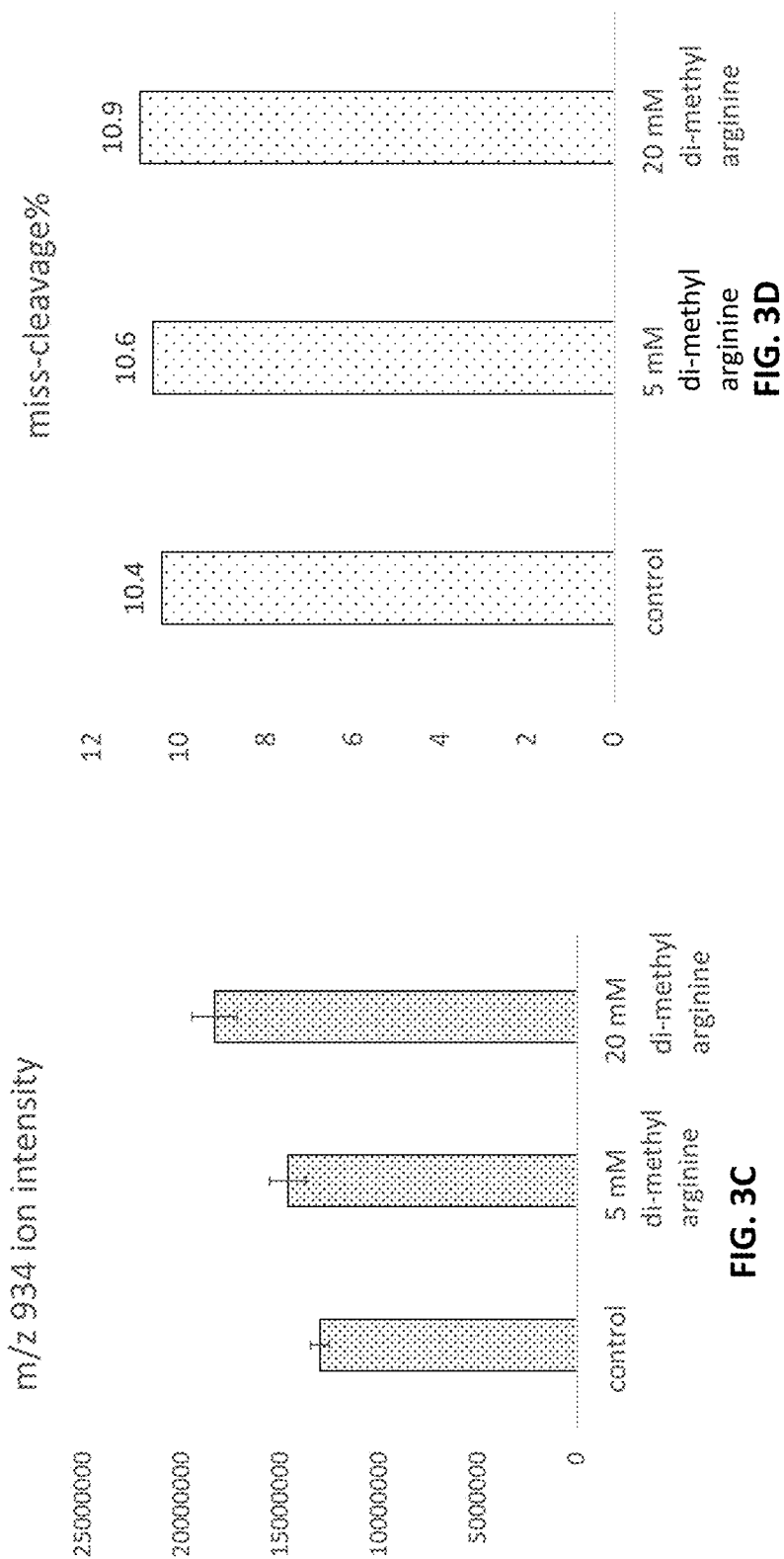

METHODS FOR HEAT-ASSISTED ENZYME DIGESTION

CROSS-REFERENCE TO RELATED APPLICATIONS

This application is a continuation-in-part of U.S. Non-Provisional patent application Ser. No. 17/314,541 filed on May 7, 2021, entitled "Methods for Heat-Assisted Enzyme Digestion." U.S. Non-Provisional patent application Ser. No. 17/314,541 claims priority and benefit to U.S. Provisional Patent Application No. 63/022,056 filed on May 8, 2020, entitled "Methods for Heat-Assisted Enzyme Digestion." The content of both applications are incorporated herein by reference in their entirety.

FIELD OF THE TECHNOLOGY

The present disclosure relates to methods for heat-assisted biomolecule sample processing, e.g., digestion and affinity ligand purification. More specifically, the present disclosure relates to the use of a coating, such as a hetero-functional coating, for conjugating biomolecules on a solid support surface in combination with heat for sample processing (e.g., clean up, sample release) for bioanalysis and the use of digestion buffers.

BACKGROUND

Biomolecules are complex molecules, which require complex workflows for analysis. These complex workflows involve numerous steps including various sample preparation steps, such as, sample clean up and protein digestion. Obtaining substantially complete digestion while not effecting sample quality (e.g., not introducing byproducts which require additional cleanup) is challenging. For example, some enzymes used in digestion when used in solution can become unstable, leading to byproducts. Conducting the digestion at elevated temperatures can improve the throughput of workflow. However, enzymes are most often effective within a specific temperature range due to denaturation or other conformation change induced by the heat. But at the specific temperature range of the enzyme, autolysis of the protein can be dramatically increased. Additionally, the hardware for the source of heat can be difficult to benchmark and assess for reproducibility.

SUMMARY

In general, the present disclosure relates to methods, techniques, and kits for heat-assisted biomolecule sample processing. Methods, techniques and kits of the present technology are used to obtain substantially complete digestion while not effecting sample quality (e.g., do not introduce byproducts which require additional cleanup).

In embodiments, immobilization of the digestion enzymes helps with their stability (i.e., prevent byproducts from forming). The methods, techniques and kits of the present disclosure differ from conventional techniques used to immobilize enzymes in that secondary interactions with the surface of the support (e.g., immobilization solid support) are minimized, greatly reduced, or eliminated.

With the immobilized enzymes, the digestion temperature can be increased. And the drawbacks associated with elevated temperatures can be reduced. The result is increased workflow without sacrificing the quality of the digestion.

With the digestion buffer, components are selected to ensure sufficient recovery of an analyte of interest, such as a protein or peptide, while reducing and/or preventing method-induced oxidation.

In general, the present disclosure is directed to a fast digestion method assisted by heat to efficiently complete digestion in minutes while providing high-fidelity peptide profiles, which is reliable and suitable for biology research or protein therapeutics characterization in a regulated environment. High-fidelity is defined as the digestion workflow results that provide >95% sequence coverage, <10% miss-cleavage, comparable modification (approximately <5% and in some examples less than 1% of heat-induced modification after digestion conducted at 25-100° C.) for therapeutic proteins in comparison to conventional in-solution digestion workflow.

The high-fidelity digestion workflow is used for peptide mapping, disulfide bond mapping, middle-up, middle-down, bottom-up proteomics, protein identification, protein quantification, bioanalysis, other digestion-related applications, or other applications (e.g., applications using affinity ligands). The method is comprised of heat-stable enzyme(s), digestion buffer (or other types of buffers), heat source, and steps to get sample ready for downstream analysis (fluorescence, UV, LC-MS detection) either through clean-up or reaction quenching.

The present disclosure provides a kit for sample preparation including a solid support surface with a polymer coating covering the solid support surface, wherein the polymer coating reduces undesired interactions between a sample and the solid support surface, a container containing a buffer comprising arginine with a maximum concentration of about 20 mM and methionine ranging in concentration from about 100 mM to about 300 mM, and a vessel for containing the solid support surface and the buffer. In some embodiments, the buffer is in-solution. In some embodiments, the buffer further includes Tris-HCl ranging in concentration from about 50 mM to about 200 mM. In some embodiments, the Tris-HCl concentration is about 100 mM. In some embodiments, the buffer further includes $CaCl_2$ ranging in concentration from about 1 mM to about 50 mM. In some embodiments, the $CaCl_2$ concentration is about 100 mM. In some embodiments, the buffer further includes a polyol, wherein the polyol is selected from the group consisting of xylitol, glycerol, propylene glycol, and butanediol. In some examples, a polyol is used to enhance stabilization for the buffer. Without wishing to be bound by theory, it is believed that polyols are not easily broken down by bacteria or metabolized to acids, thereby enhancing stability of the buffer in-solution even at elevated temperatures. In some embodiments, the polyol is xylitol and the concentration of xylitol ranges from about 600 mM to about 680 mM. In some embodiments, the concentration of xylitol ranges from about 650 mM to about 660 mM (e.g., xylitol concentration can be 657 mM). In some embodiments, the methionine ranges in concentration from about 100 mM to about 300 mM. In some embodiments, the methionine concentration is about 200 mM. In some embodiments, the polymer coating includes two portions, a first coating portion with functionality for bioconjugation and a second coating portion with a functionality to reduce the undesired interactions between the protein and the solid support surface. In some embodiments, the polymer coating provides a surface coverage of at least 5 µmol/m². In some embodiments, the kit further includes a heat source to assist the protein sample preparation.

The present disclosure provides a kit for sample preparation, the kit including a solid support surface with a polymer coating covering the solid support surface, wherein the polymer coating reduces undesired interactions between the sample and the solid support surface, a buffer (e.g., buffer in a container, such as a vial) comprising arginine and an oxidation scavenger, wherein the ratio of arginine to the oxidation scavenger ranges from about 1:15 to about 1:30, and a vessel for containing the solid support surface and the buffer. In some embodiments, a maximum concentration of the arginine is about 20 mM. In some embodiments, the oxidation scavenger is methionine. In some embodiments, a concentration of the methionine ranges from about 100 mM to about 300 mM. In some embodiments, the ratio of arginine to the oxidation scavenger is about 1:20. In some embodiments, the buffer further includes Tris-HCl, $CaCl_2$, and xylitol. In some embodiments, the polymer coating includes two portions, a first coating portion with functionality for bioconjugation and a second coating portion with a functionality to reduce the undesired interactions between the protein and the solid support surface. In some embodiments, the polymer coating provides a surface coverage of at least 5 µmol/m². In some embodiments, the kit further includes a heat source to assist the protein sample preparation.

The present disclosure provides methods for conducting fast enzyme digestion with the assistance of heat. The fast digestion method can be used for protein/peptide analysis. In general, the method includes one or more of the following: heat-stable enzyme(s), digestion buffer, heat source, and steps to set sample ready for downstream analysis (fluorescence, UV, LC-MS detection) either through clean-up or reaction quenching. For example, some of the methods include the followings components: the immobilized enzyme on a solid support with superior heat stability and a hydrophilic characteristic that minimizes non-specific binding; the digestion buffer that supports the kinetics of enzyme (such as trypsin) activity at elevated temperature while also minimizing the heat-induced modification on peptides; the apparatus (e.g., vials, plates or columns) ensures maximum heat transfer efficiency with minimal non-specific binding.

The buffer may need to be heat stable due to the heat assistance for conducting fast enzyme digestion. Without wishing to be bound by theory, in some embodiments, the buffer includes a polyol to enhance heat stability of the buffer. Depending on the heat stability requirements among other factors, the polyol and the concentration of that polyol can be varied. Some examples of polyols include xylitol, erythritol, glycerol, propylene glycol, and butanediol.

In some embodiments, the buffer includes a buffering agent selected from the group consisting of Tris, BIS-Tris, 2-ethanesulfonic acid (MES), HEPES, triethanolamine, and trimethylamine. The buffer via the buffering agent can contain divalent ions such as $CaCl_2$. The buffer in-solution can also contain polyols selected from a group consisting of, and not limited to, glycerol, xylitol, propylene glycol, butanediol or erythritol. In some embodiments, the buffer in-solution includes xylitol and $CaCl_2$. In some embodiments, the buffer in-solution includes, or consists only of, Tris-HCl, $CaCl_2$, xylitol, arginine, and methionine.

BRIEF DESCRIPTION OF THE DRAWINGS

The technology will be more fully understood from the following detailed description taken in conjunction with the accompanying drawings, in which:

FIG. 3C is a graph illustrating the effect on hydrophobic peptide recovery of adding dimethyl-arginine to a digestion buffer. FIG. 3D is a graph illustrating the effect on digestion efficiency of adding dimethyl-arginine to the digestion buffer.

FIG. 19A is a graph illustrating the effect on hydrophobic peptide recovery of adding arginine to a digestion buffer. FIG. 19B is a graph illustrating the effect on digestion efficiency of adding arginine to the digestion buffer.

FIG. 20A is a graph illustrating the effect on oxidation percentage (%) of adding methionine to a digestion buffer. FIG. 20B is a graph illustrating the effect on peptide recovery of adding methionine to the digestion buffer.

DETAILED DESCRIPTION

Figure 1:
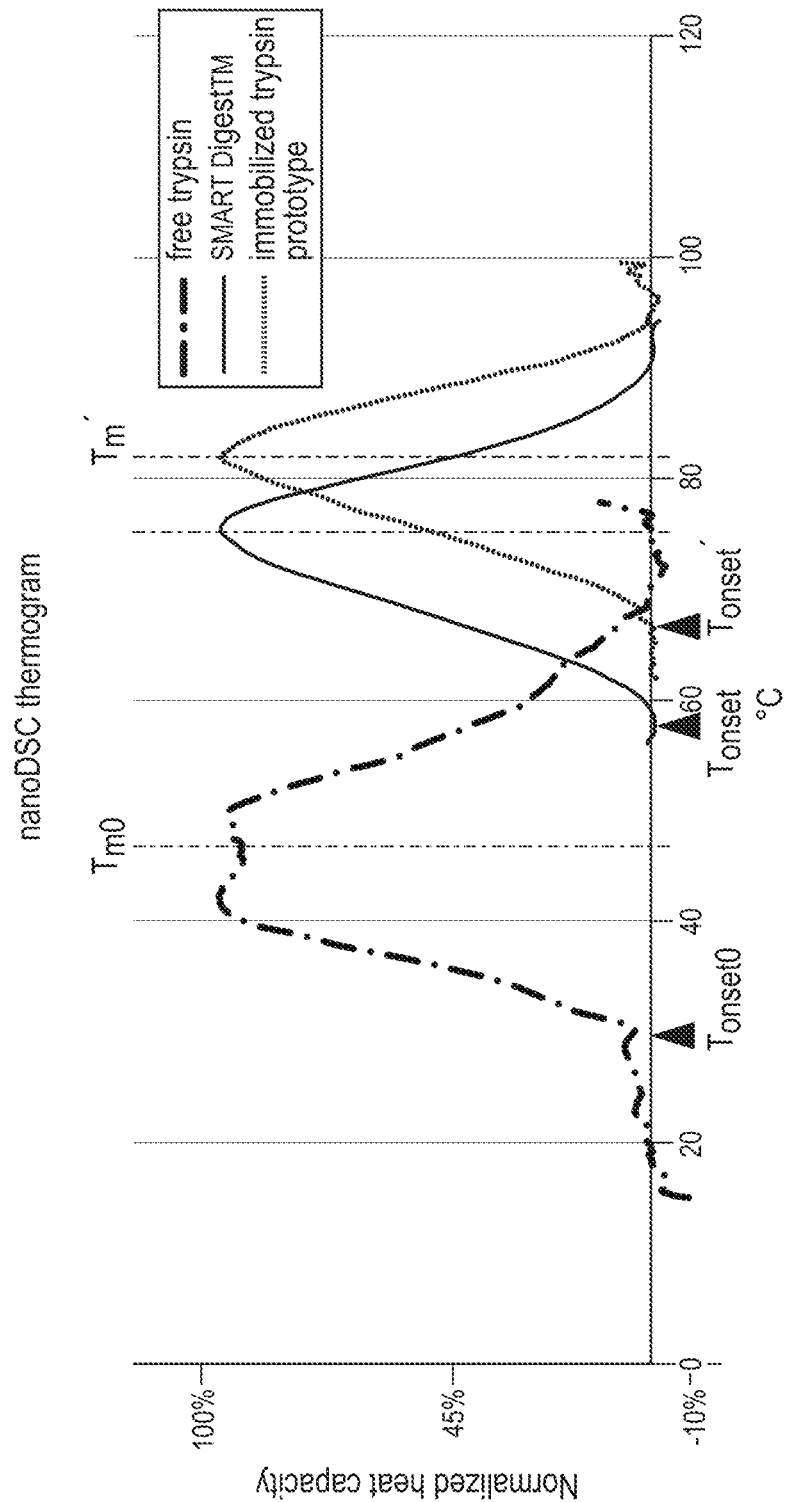
FIG. 1 is a graph of thermograms in accordance the present disclosure.

Conducting protein digestion at elevated temperature has been problematic because of incompleteness of the digestion, nonspecific binding to the resin, and heat-induced modifications on peptides compared to traditional in solution digestion that often carried out at 37° C. Through engineering an immobilized enzyme with a specific surface chemistry, the present disclosure facilitates a workflow that generates a highly similar profile as in-solution digestion but only requires minutes of digestion. The digestion buffer has been tailored to increase peptide recovery and enzyme activity.

Of note, the digestion completeness of the present disclosure is 90-95%, much higher compared to the leading competitor product SMART Digest™ (a protein digestion kit available from Thermo Fisher Scientific, Waltham, MA) which is only 65%-70%. The non-specific binding effect of peptides is reduced by 10-30% using the technology of the present disclosure compared to Smart Digest™. The present disclosure is also amenable to reducing/alkylating reagents while Smart Digest™ is not compatible.

Enzyme digestion of proteins is widely adopted in the biochemistry research community, where the resulted peptides could inform on the amino acid modification or the abundance of the protein in a relevant physiological environment. With the emergence of antibody therapeutics in biopharmaceutical industry, this technique has proved its value in the bioprocess and quality control evaluations to support the identification and monitoring of critical quality attributes that reflect the purity and safety profiles of a particular therapeutic. However, the digestion of a large protein, e.g. an antibody with 150 kDa molecular weight, takes hours to complete and oftentimes requires optimization on many experimental parameters including incubation time, temperature, and protein to enzyme ratios. This lengthy process has restricted the throughput where timely decisions often need to be made either in the discovery phase or in the manufacturing process. Another caveat of the process is the lengthy digestion process could induce artificial modification on the proteins or peptides, adding extra work in defining those modifications. In the case of trypsin digestion, autolysis along with time could result in unfavorable interference for downstream analysis.

Attempts to increase the throughput of the workflow have inspired some recent advances in automating the workflow. Liquid handlers now can simultaneously process 96 or even 384 samples at one time, however the time for digestion itself still requires hours. On the other hand, the most common downstream peptide analysis requires a 60-120 minute gradient of liquid chromatography to achieve sufficient separation, so there is a maximum of 24 samples that can be processed a day. Excess number of samples queued in line may suffer from potential loss of peptides due to stability or adsorption issues. This would in turn affect the consistency and accuracy of the platform assay.

Attempts to conduct digestion at elevated temperature also have been investigated. The rationale behind is that enzyme reaction, just like any other chemical reaction, follows the rule of the Arrhenius equation (Equation 1):

$$k = Ae^{\frac{-Ea}{RT}} \quad (1)$$

Where k is the kinetic rate constant for the reaction, A is the Arrhenius constant, G is the standard free energy of activation (kJ $M^{-1}$) which depends on entropy and enthalpy factors, R is the gas law constant and T is the absolute temperature. Typical standard free energies of activation (15-70 kJ $M^{-1}$) give rise to increases in rate by factors between 1.2 and 2.5 for every 10° C. rise in temperature. But usually the enzyme would be most effective within a preferred temperature range due to denaturation or other conformation change induced by heat. Using sequencing grade trypsin as an example, the preferred temperature is 50-55° C. for a 1-hour digestion experiment on casein. However, at such temperature the autolysis of trypsin has dramatically increased along with time which resulted in a 60% activity loss within 2 hours.

The heat source can be a heat source that provides uniformity (uniform heat transfer) and even heat distribution. In the example of immobilized enzyme, agitation of a dispersive device or flow though mode interaction with protein needs to be ensured to achieve a homogenous or even contact. The ramp time that the heat source can provide is also a factor when selecting the heat source. A short ramp time is advantageous. In the dispersive immobilized enzyme format, 5 minutes or less time is used to reach to the determined digestion temperature for a 10-minute digestion. In one example of immobilized trypsin, 5 minutes or less to reach to 75° C. and maintain the temperature at 75° C. is preferred.

In some examples, heat source can be anything that supports consistent heating at 50-100° C. for 5 minutes or longer. Some examples include an oven, incubator, rocker, or thermomixer. In some examples, to achieve consistent and best result Eppendorf ThermoMixer C (based on Peltier technology) can be used, preferably with the option of a heated lid. The heated lid can be helpful for digestions that take a long time (e.g., over 30 minutes).

Efficient heat transfer between the consumable and heat source is also a factor when selecting the heat source. In one example of dispersive immobilized trypsin, the thickness of consumables used correlated with their digestion performance. The preferred temperature depends on the enzyme or combination of enzymes selected. In the example of immobilized trypsin, a $T_m$ and onset temperature ($T_{onset}$) can help determine at what temperature is most appropriate for a heated digestion. The preferred temperature for trypsin is between $T_{onset}$ to $T_m$.

Microwave-assisted and infrared-assisted enzyme digestion appeared to improve the kinetics of digestion by shortening the time to as little as 5 min, however these studies were mostly helpful for small to medium size proteins (below 100 kDa) and the quality of the digested products have not been rigorously evaluated. Moreover, hardware like microwave as the source of heat is simply difficult to benchmark and assessed for reproducibility.

Immobilized enzyme in dispersive format, or in column/cartridge format are also commercially available. The advantage of immobilization is to improve the heat-stability by restraining the denaturation effect of heat so that digestion could be completed at a higher temperature within a shortened period of time. However, by far the reported workflows could only achieve limited digestion efficiency (the percentage of all tryptic peptides vs. total peptides detected) varying from 30% to 80% among proteins compared to in-solution digestion. Most protocols associated with immobilized enzyme advocated the elimination of pretreatment (denaturation, reduction and alkylation), claiming sufficient denaturation achieved by heat. However, this only applies to proteins are small or prone to heat denaturation, since the incomplete digestion for larger proteins or proteins with multiple disulfide bonds will not be efficiently denatured by heat. Moreover, the extent of heat-induced modification and the reproducibility of these innovations that have rarely been evaluated rigorously and extensively.

Figure 18:
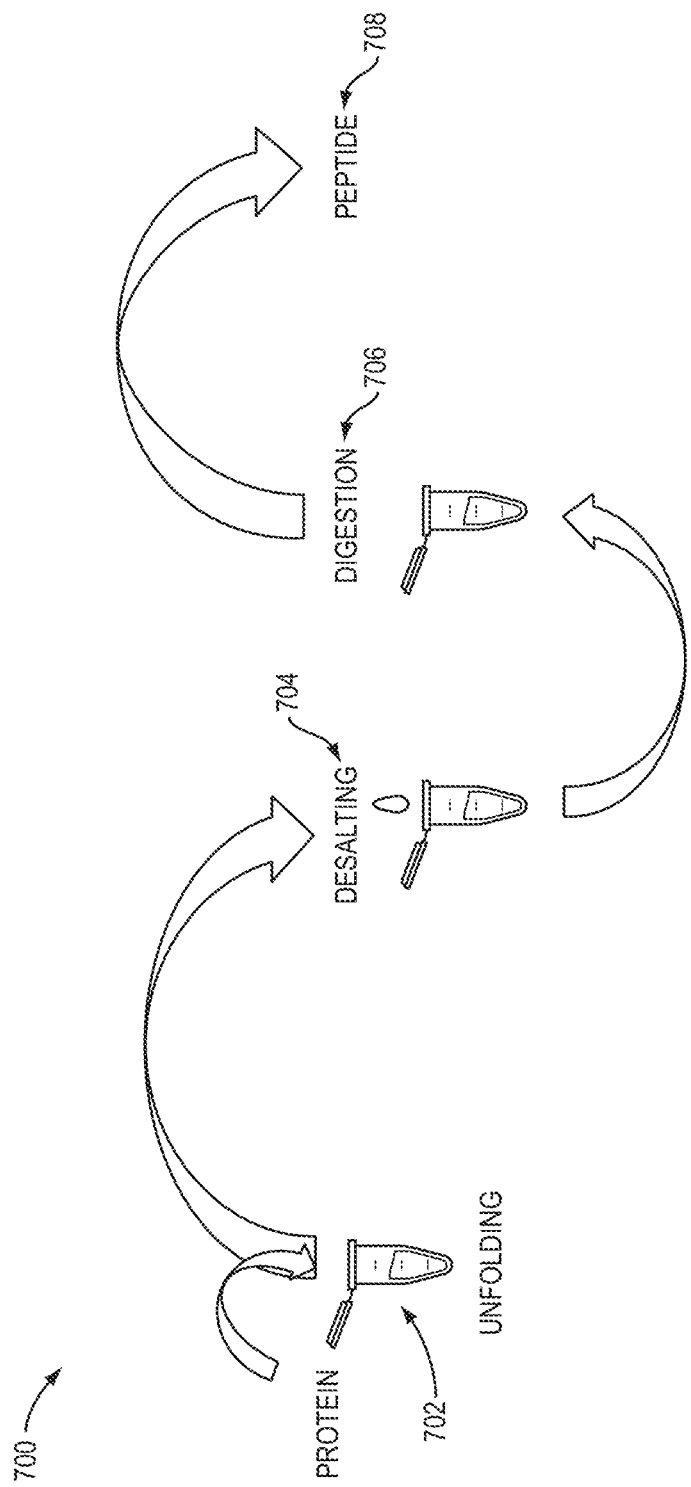
FIG. 18 is a flowchart of an example of trypsin digestion current workflow.

FIG. 18 is a flow chart illustrating the peptide mapping workflow 700. In some examples, peptide mapping workflow 700 includes four parts. A part one 702 includes a sample with an analyte of interest, such as a protein, is unfolded. A part two 704 includes desalting the sample, which includes the unfolded analyte of interest. A part three 706 includes digesting the analyte of interest of the sample. Here, the device used in digesting the analyte of interest includes a hetero-functional coating of the present disclosure. After the analyte of interest is digested, a part four 708 includes collecting the sample with digested analyte of interest.

In some examples, part one 702 and part two 704 can be dependent on the analyte of interest. For example, part one 702 and part two 704 can be considered pre-treatment steps and may not be required based on the analyte of interest, such as a protein.

A desired fast digestion method assisted by heat would efficiently complete digestion in minutes while providing high-fidelity peptide profiles, which would be reliable and suitable for either biology research or protein therapeutics characterization in a regulated environment. High fidelity in this context is interpreted as the results of the digestion workflow provide >95% sequence coverage, <10% miss-cleavage, comparable modification % (usually <5%) for therapeutic proteins in comparison to conventional in solution digestion workflow. This disclosure provides the methods for conducting fast enzyme digestion with the assistance of heat. The methods comprise essentially the following components: the immobilized enzyme on a solid support with superior heat stability and a hydrophilic characteristic that minimizes nonspecific binding; the digestion buffer that supports the kinetics of trypsin activity at elevated temperature while also minimizes the heat-induced modification on peptides; the apparatus (vials, plates or columns) that ensures the maximum heat transfer efficiency with minimal nonspecific binding.

The present disclosure provides the enhanced methods for conducting fast enzyme digestion with the assistance of heat. The methods comprise essentially the following components: The immobilized enzyme on a solid support with superior heat stability and a hydrophilic characteristic that minimizes nonspecific binding; the digestion buffer that supports the kinetics of trypsin activity at elevated temperature while also minimizes the heat-induced modification on peptides; The apparatus (vials, plates or columns) that ensures the maximum heat transfer efficiency with minimal nonspecific binding. The complete digestion workflow starts with desaturating proteins in 8M guanidine or 6M urea. After reduction and alkylation, the proteins are desalted and subject to digestion. The digestion mixture is composed of immobilized enzyme, proteins in digestion buffer at beneficial concentrations. Relevant factors for the digestion buffer can be temperature, pH, metal concentration, and additives.

The buffer of the present disclosure can include a buffering agent to control pH, protein sample dispersant and metal ions. The metal ions can be divalent metal ions, preferably $Ca^{2+}$. The buffering agent can include Tris, BIS-Tris, MES, HEPES, Triethanolamine, and trimethylamine. The protein sample dispersant can be chosen from a group of polyols such as glycerol, xylitol, propylene glycol, butanediol or erythritol. The metal ions and protein sample dispersant can be additives in the buffer. For example, $CaCl_2$, methionine, xylitol, and/or glycerol can be additives in the buffer.

After digestion the immobilized enzyme are removed either through centrifugation or filtration. Peptides are recovered as supernatants and submitted to downstream analysis, either LC-UV or LC-MS.

An immobilized enzyme (or in some examples an affinity ligand) on the coating, as described in more detail in U.S. patent application Ser. No. 17/314,853, entitled "Heterofunctional coating for conjugating biomolecules on a solid support and use thereof for bioanalysis", provides heat stability. (U.S. application Ser. No. 17/314,853 is herein incorporated by reference in its entirety.) As for digestion, chemical immobilization methods through a covalent interaction approach stand out since this would ensure the least enzyme leakage, and more importantly, better heat stability. Many of these immobilized enzymes are provided in a column format which often requires multi-dimensional LC systems for operation. The working temperature varies from 37° C. to 60° C. and there is a lack of information on their lifetime and reproducibility. One notable commercially available product in a dispersive format is Smart Digest™ which has adopted a working temperature at 70° C.

FIG. 1 is a graph of thermograms in accordance with aspects of the present disclosure. Specifically, FIG. 1 displays NanoDSC thermograms of free trypsin, Smart Digest™ trypsin, and one preferred immobilized enzyme (e.g., trypsin) prototype (e.g., silica-based solid support with coating in accordance with the present technology), where $T_m$—temperature where half of the protein is unfolded and $T_{onset}$—temperature where protein starts to unfold. For example, the prototype (i.e., silica-based solid support with coating) with immobilized trypsin showed even better thermostability compared to Smart Digest™ (FIG. 1).

Figure 2:
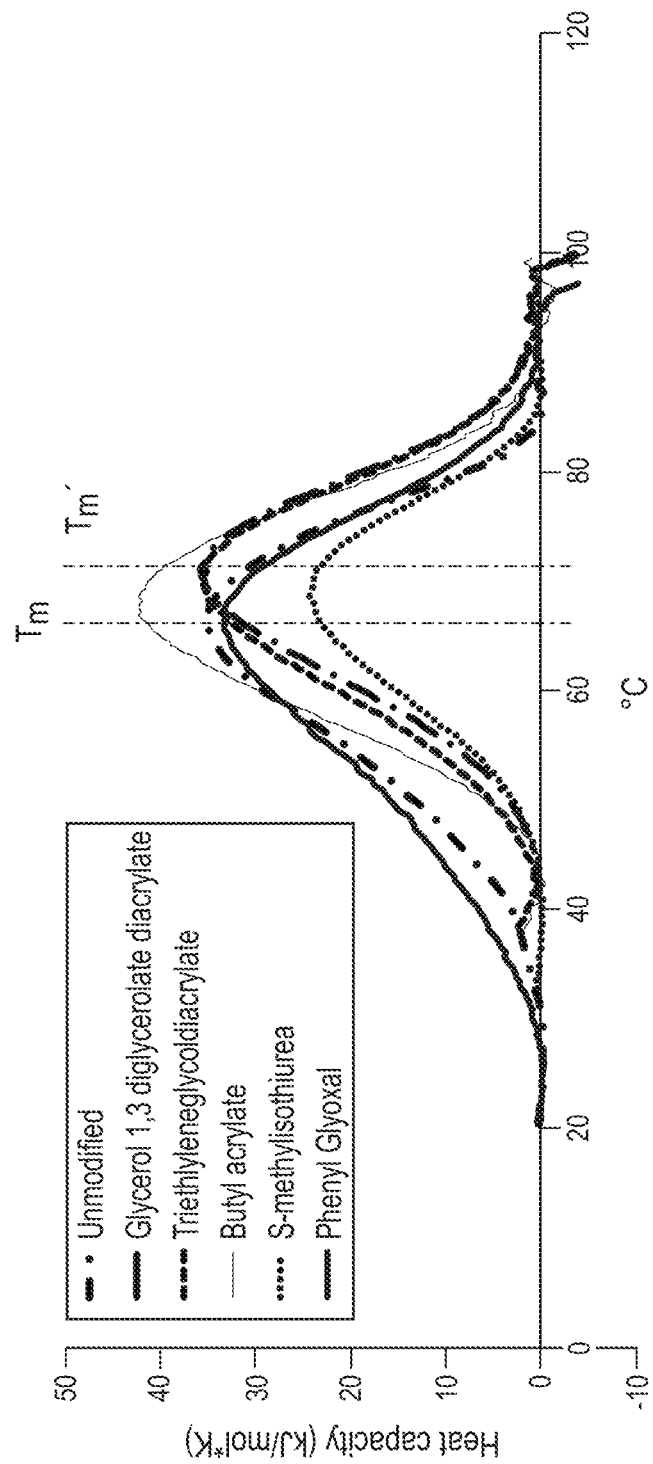
FIG. 2 is a graph of thermograms in accordance the present disclosure.

FIG. 2 is a graph of thermograms in accordance with aspects of the present disclosure. FIG. 2 displays NanoDSC thermograms of immobilized enzyme prototypes with different modification. The unmodified tryspin has a $T_m$ around 65° C. The point modified trypsin (butyl acrylate, s-methylisothiurea and phenyl glyoxal have slightly improved $T_m$ for 1-2° C., while crosslinker modified trypsin (glycerol 1,3 diglycerolate diacrylate and triethlyleneglycoldiacrylate) has significantly improved $T_m$ for 5-7° C. To further increase the heat stability of trypsin, crosslinkers that nonspecifically react with amines could restrain the structural change under heat (FIG. 2). Similarly, modifiers that covalently bound with a certain amino acid that are not at the active sites also could create steric hindrance during heat denaturation (FIG. 2).

Figure 4:
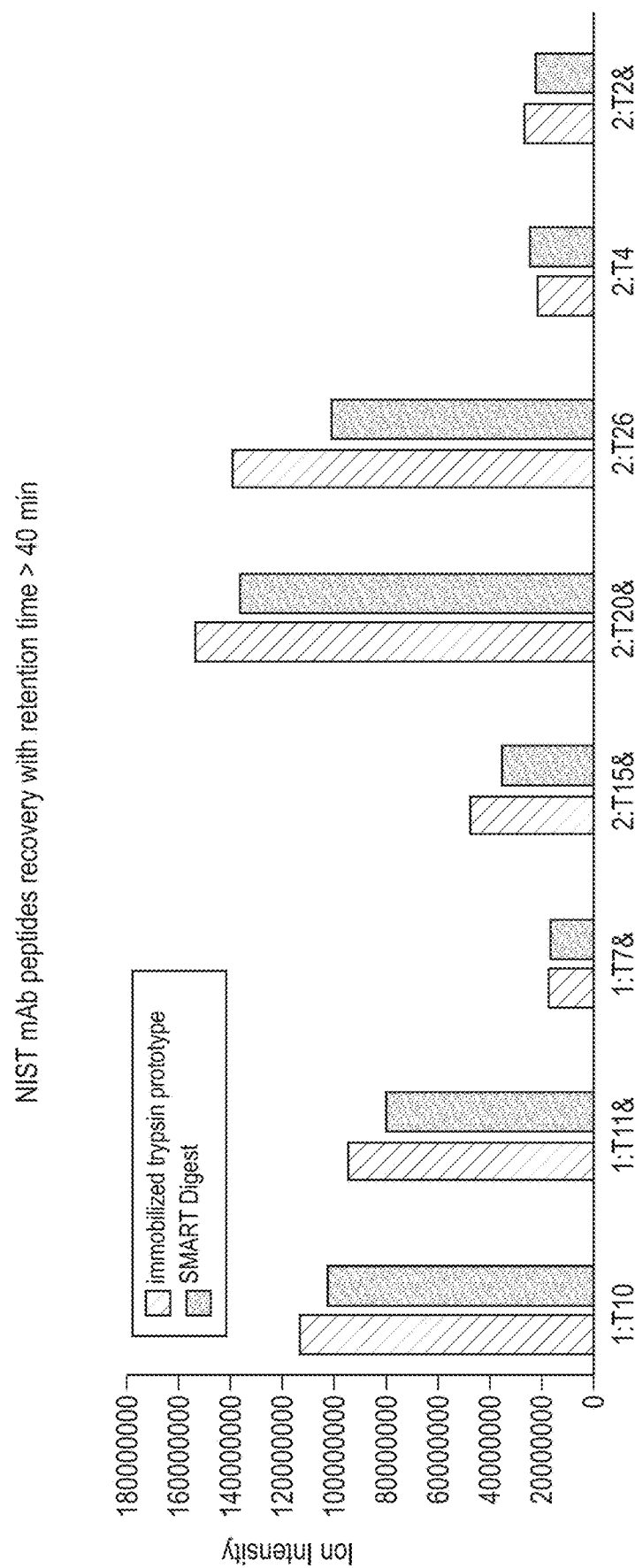
FIG. 4 is a graph of a recovery of a mixture of hydrophobic peptides after incubation with immobilized enzymes in accordance with the present disclosure.

The immobilized enzymes on the support impart enhanced surface characteristics, such as nonspecific binding, conjugation chemistry, and digestion efficiency. The solid support can be composed of a hydrophilic surface with porous structure that could minimize non-specific binding, which in turn would ensure the digestion efficiency and the recovery of peptides. Important physical parameters include the particle size and pore size of the solid support, which affect the diffusion of proteins into the pores and how much access they have to the enzyme. For a selected material, hydrophilic modification is optimized so that the nonspecific binding could be tuned to a preferred level. FIG. 4 is a graph of a recovery of a mixture of hydrophobic peptides after incubation with immobilized enzymes in accordance with the present disclosure. FIG. 4 demonstrate the recovery % of hydrophobic peptides after mixed with selected immobilized support for only 5 minutes.

In some examples, the solid support is porous and the pore size ranges from about 50 to about 5000 Å. The pore size can affect the diffusion of the protein into the pores and how much access the protein has to the enzyme.

The solid support surface can be a plurality of particles, each particle having a particle size ranging from about 1 to about 200 microns. The particle size can affect the diffusion of the protein and how much access the protein has to the enzyme. The solid support is the material for immobilizing the enzymes. In some examples, the consumable used for containing the reaction components includes a multi-well plate, a vial, or a column. The consumable be coated to alleviate non-specific binding.

Figure 5:
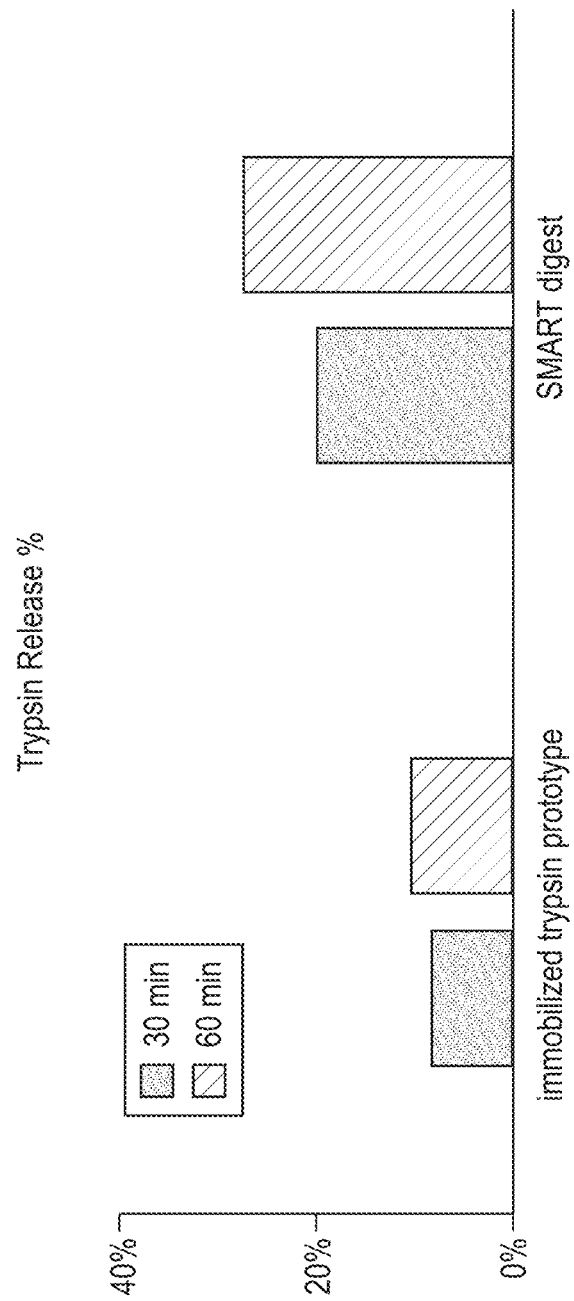
FIG. 5 is a graph of released trypsin after incubated in digestion buffer at 70° C.

Another consideration on immobilization is how stable the enzyme is conjugated on the support. The released enzyme usually has significantly reduced thermal stability at elevated temperature and with less enzyme immobilized on the support, the digestion efficiency would decrease along with time. Worse still, in the case of trypsin, it can contribute to significant noises to downstream analysis with the autolysis products if UV analysis is employed for downstream analysis. FIG. 5 is graph of released trypsin after incubated in digestion buffer at 70° C. A preferred product has minimal leakage of the enzyme during the digestion (FIG. 5).

In some examples, immobilized trypsin does not show autolysis at low temperature (25-45° C.), very low autolysis (less than 1%) at temperatures above 65° C. at pH greater than 7, and no autolysis at lower pH.

The immobilized enzyme can include one enzyme or combination of enzymes (e.g., trypsin, chymotrypsin, Lys-C, Glu-C, Arg-C, Asp N, papain, pepsin, elastase, IdeS, pronase and PNGase) could be immobilized on particle, chip, surface that could sustain certain elevated temperature within 25-110° C. and do not negatively affect enzyme activity. In some examples, elevated temperature range may be further narrowed for heating to occur at an elevated temperature ranging above 45° C. preferably 65° C. to 75° C. and not greater than 85° C. Enzyme can possess heat stability through the immobilization process. In the example of trypsin, melting temperature (Tm) can be by increased 30-50° C. after immobilization. Modification of trypsin through point modification and crosslinking and conjugating small polymers or ligands can further increase Tm. In some examples, the solid support with the immobilized enzyme has less than 30% non-specific binding for all protein/peptides present during digestion, and the immobilized enzyme can be stable with leaching less than 20% during the digestion procedure.

In some examples, the modified enzyme is in-solution. The enzyme can include one enzyme or a combination of enzymes (e.g., trypsin, chymotrypsin, Lys-C, Glu-C, Arg-C, Asp N, papain, pepsin, elastase, IdeS, pronase and PNGase).

Figure 6A:
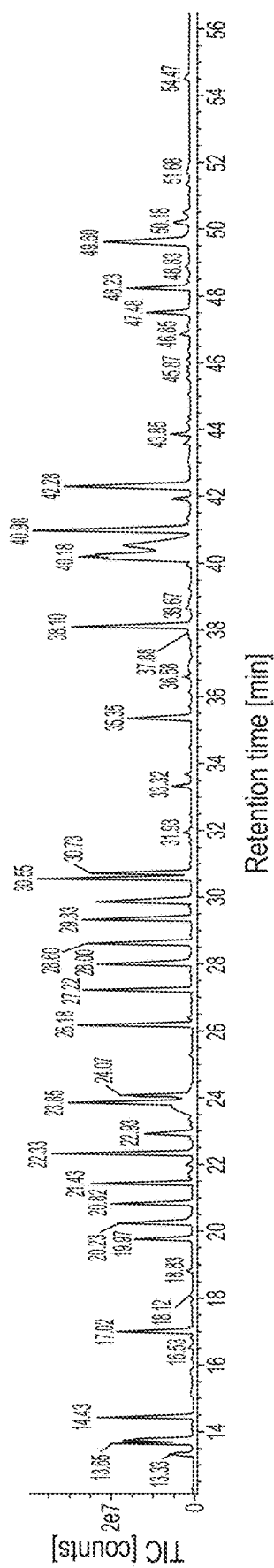
FIGS. 6A, 6B, and 6C are graphs displaying LC-MS chromatograms generated after NIST mAb digested under varying conditions.
Figure 6B:
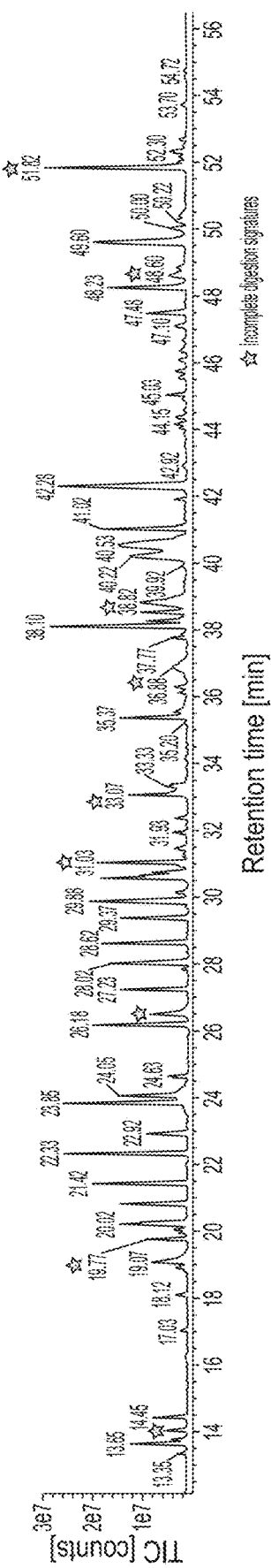
Figure 6C:
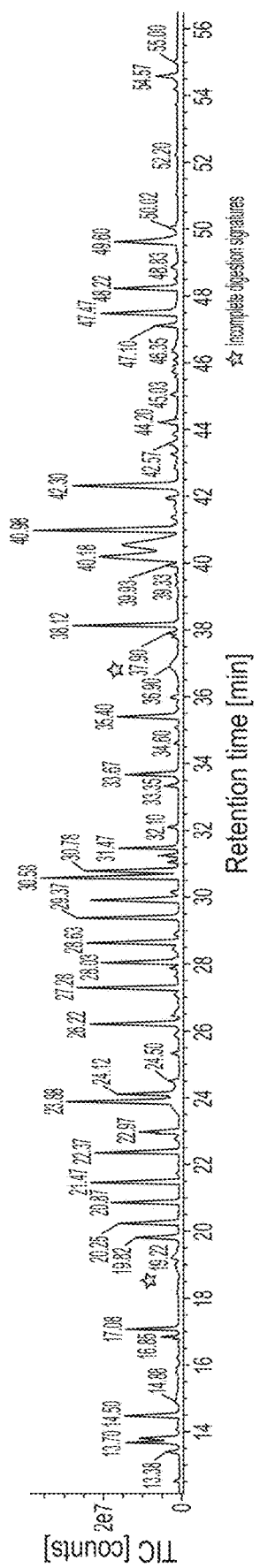
Figure 7:
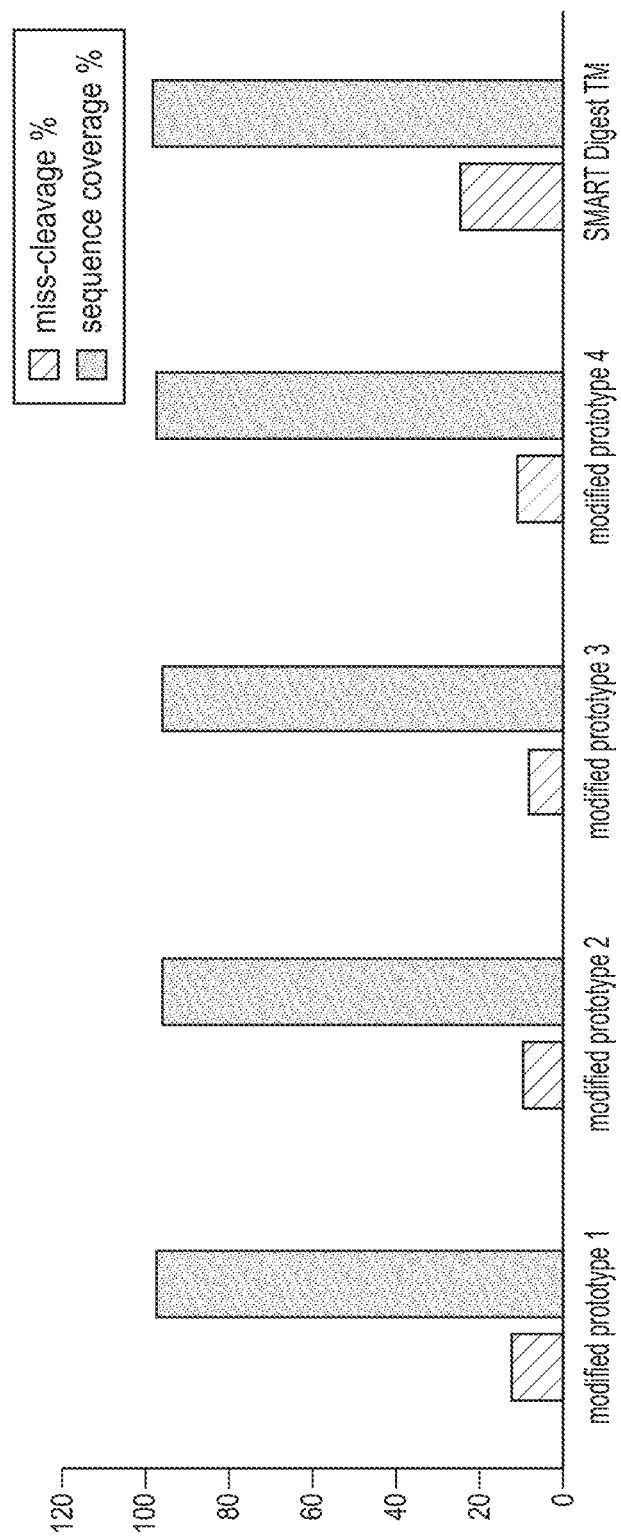
FIG. 7 is a graph displaying miss-cleavage % and sequence coverage % comparing examples in accordance with the present disclosure.

The digestion efficiency of an immobilized enzyme is a combined result of surface characteristics. Using NIST mAb as a model protein, the miss-cleavage % could reflect the digestion efficiency by weighing the ratio of tryptic peptides (with no miss-cleavage) in the total peptides detected after digestion. Reported sequence coverage for using Smart Digest™ under recommended workflow could only reach 50-76% for IgG1. FIGS. 6A, 6B, and 6C are graphs displaying LC-MS chromatograms generated after NIST mAb digested under varying conditions. Specifically, FIGS. 6A, 6B, and 6C are graphs displaying LC-MS chromatograms generated after NIST mAb digested under (FIG. 6A) two hour in solution digestion; (FIG. 6B) 10-minute Smart Digest™ digestion; (FIG. 6C) 10-minute prototype digestion. FIG. 7 is a graph displaying miss-cleavage % and sequence coverage % comparing examples in accordance with the present disclosure. Specifically, FIG. 7 displays miss-cleavage % and sequence coverage % compared among prototypes with increasing levels of hydrophilic modification and Smart Digest™. A desired prototype with improved heat stability should be capable to provide robust digestion (miss cleavage %<10%, sequence coverage>90%) under optimized condition (FIGS. 6 & 7). By tuning the hydrophilic modification on the surface, the digestion efficiency could find a "sweet spot" (FIG. 7) with a balance of digestion efficiency and mass recovery of peptides.

Before digestion, the present disclosure can include pre-treatment. Before protein digestion, there can be a pretreatment step. In some examples, proteins that can be easily denatured by heat and are introduced during digestion do not require pretreatment. For proteins that need pretreatment, denaturation followed with reduction and alkylation are common steps to fully unfold the protein.

The digestion conditions play important role for digesting an immobilized enzyme at elevated temperatures. Digestion parameters like pH, temperature and digestion time that work best with free enzyme in solution will exhibit distinctive features in a heated environment based on the selection of immobilization support. Additives can help cope with improved kinetics, heat-induced modification on peptides, adsorption of peptides onto the immobilized support and aggregation of slurry or proteins. With heat-assisted denaturation, complete digestion could be achieved without pre-treatment including denaturation with guanidine or urea, reduction and alkylation, without identifying the extent of miss-cleavage. In the present disclosure, complete digestion as the result of miss-cleavage % and is no bigger than 10%, which means the protein have been completely digested in a way that more than 90% of the resulted peptides have no miss-cleaved sites. This is a stringent criterion and also the quality that differentiates the present disclosure and the utilization of the present disclosure from others.

In the present disclosure, pre-treatment is optional depending on the analyte of interest (e.g., depending on the protein). Desalting to remove pre-treatment is optional because the resin is compatible. Pre-treatment of samples (including denaturation, reduction and alkylation) can be conducted before digestion in pursuit of high-fidelity peptide profiles. While the whole process, including pre-treatment, is no longer than 2 hours with digestion included.

Figure 8A:
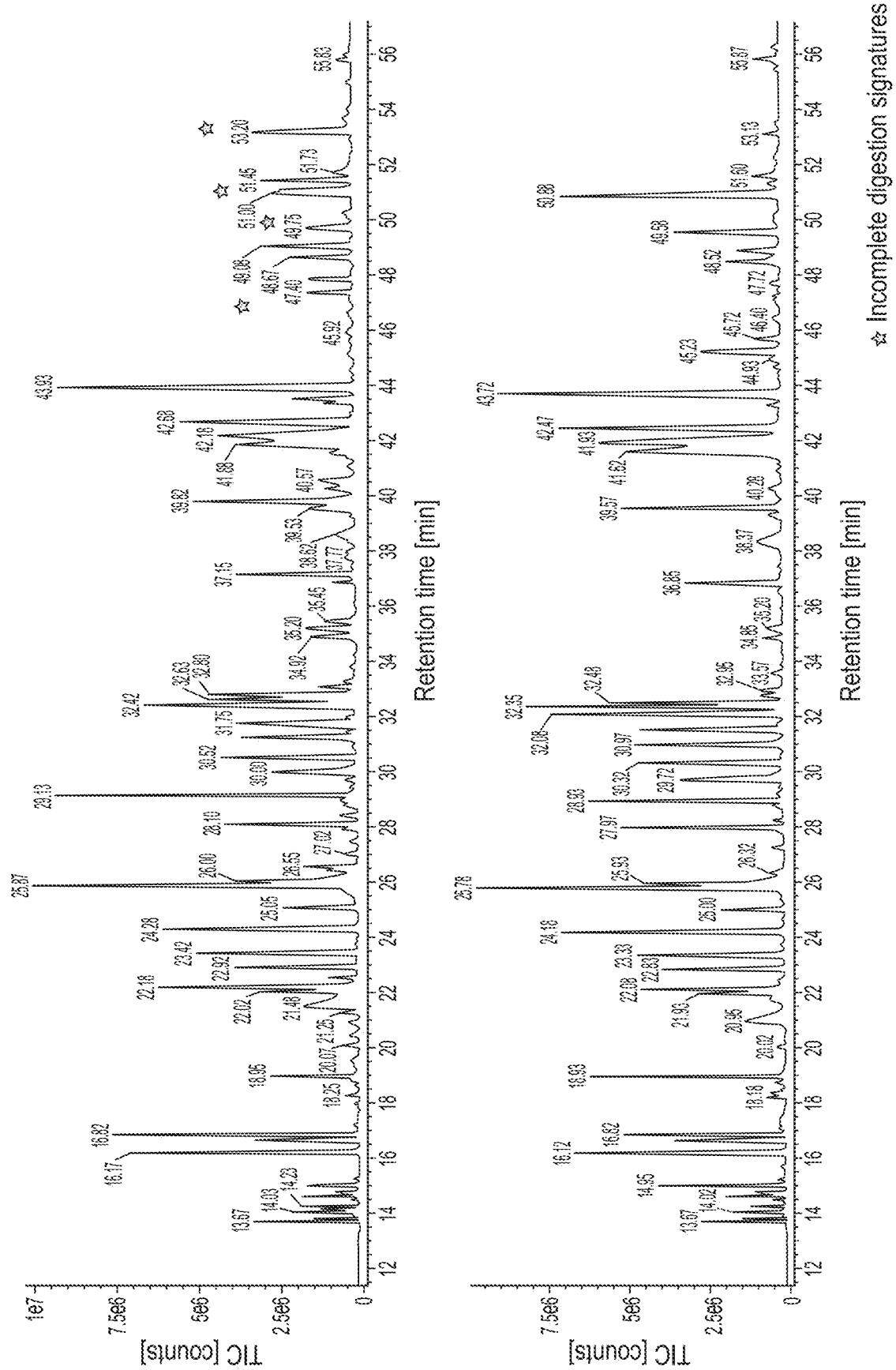
FIGS. 8A, 8B, and 8C are graphs comparing digestion examples at different temperatures.
Figure 8B:
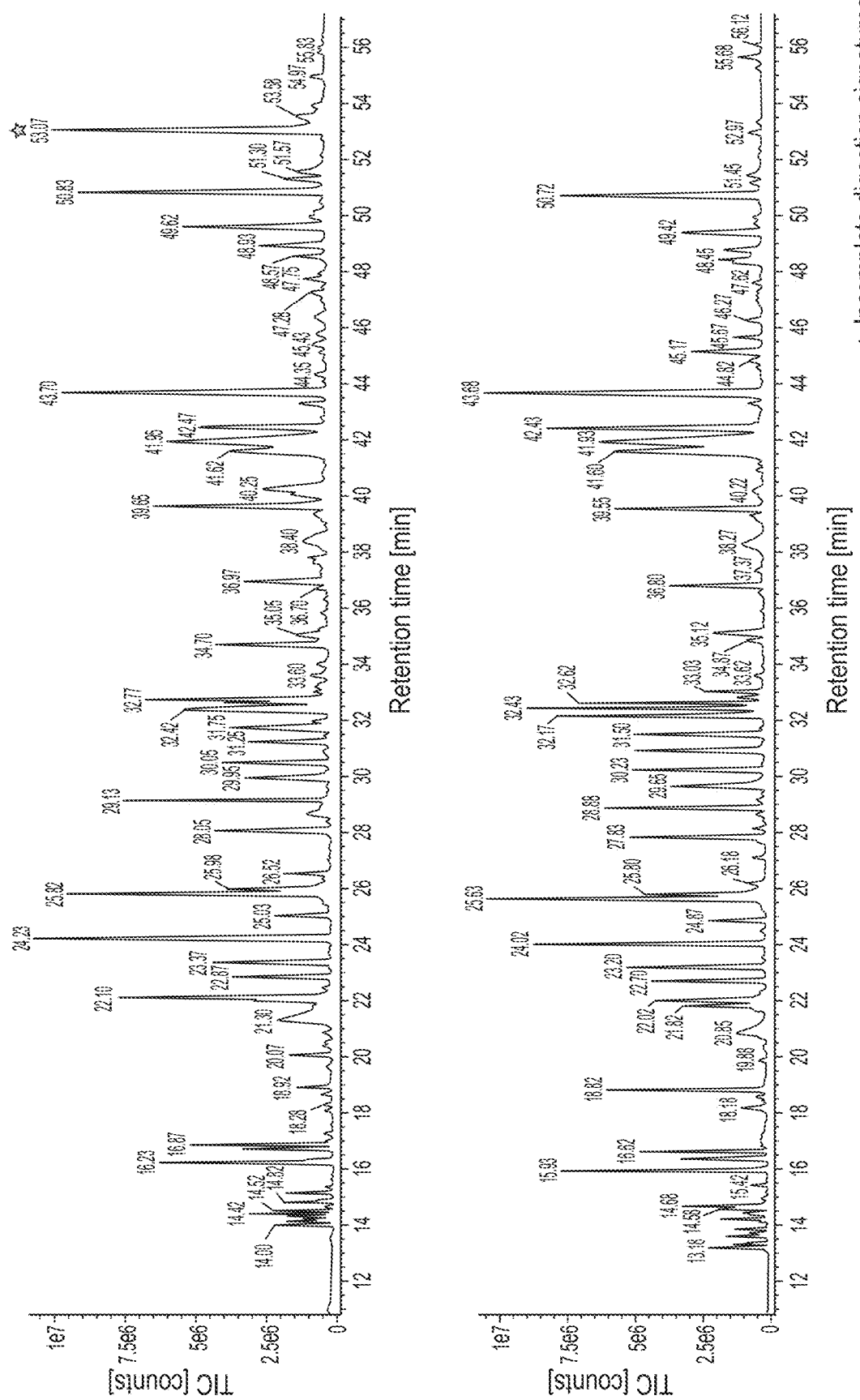
Figure 8C:
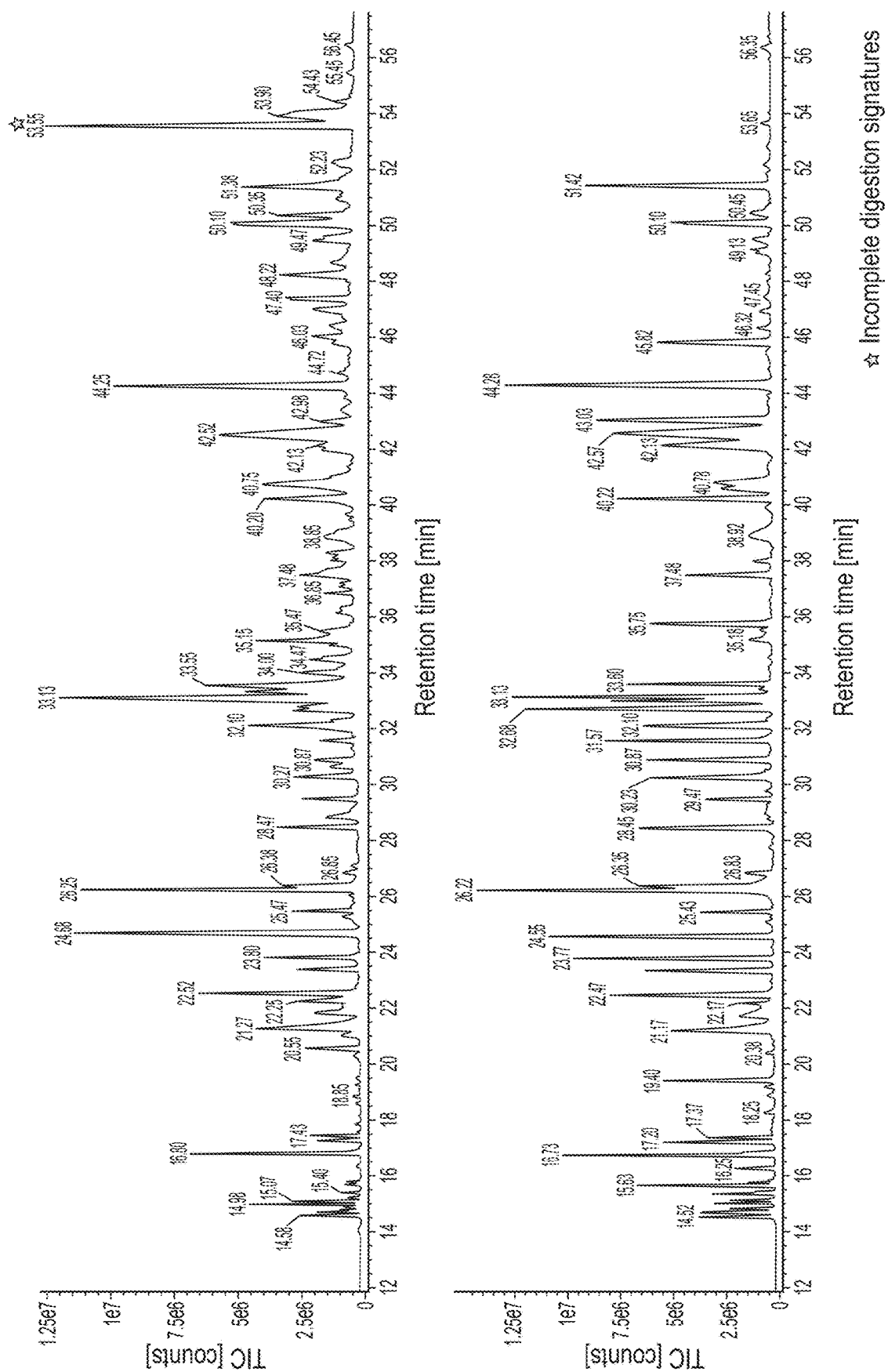

After immobilization the enzyme exhibits improved thermal stability, and a preferred temperature needs to be determined for the selected enzyme since they may exhibit distinctive correlation or no correlation between $T_m$ and temperature for maximum activity. Empirically in the case of trypsin, it's preferable to conduct digestion at 70-75° C. for 10 min which is close to its $T_m$. FIGS. 8A, 8B, and 8C are graphs comparing digestion examples at different temperatures. Specifically, FIGS. 8A, 8B, and 8C display LC-MS chromatograms comparing Smart Digest™ and immobilized trypsin after digesting NIST mAb for 10 minutes at (FIG. 8A) 60° C.; (FIG. 8B) 70° C.; (FIG. 8C) 80° C.

Lower than this temperature significant incomplete digestion would appear (FIGS. 8A-8C). Without wishing to be limited by theory, the digestion efficiency would reach a higher value at temperatures higher than 70° C., and a shortened digestion time is expected to achieve similar digestion completeness. But that also may require a slightly longer equilibration time for the reaction mixture which could give rise to heat-induced degradation or adsorption, or other unfavorable modifications.

Figure 9B:
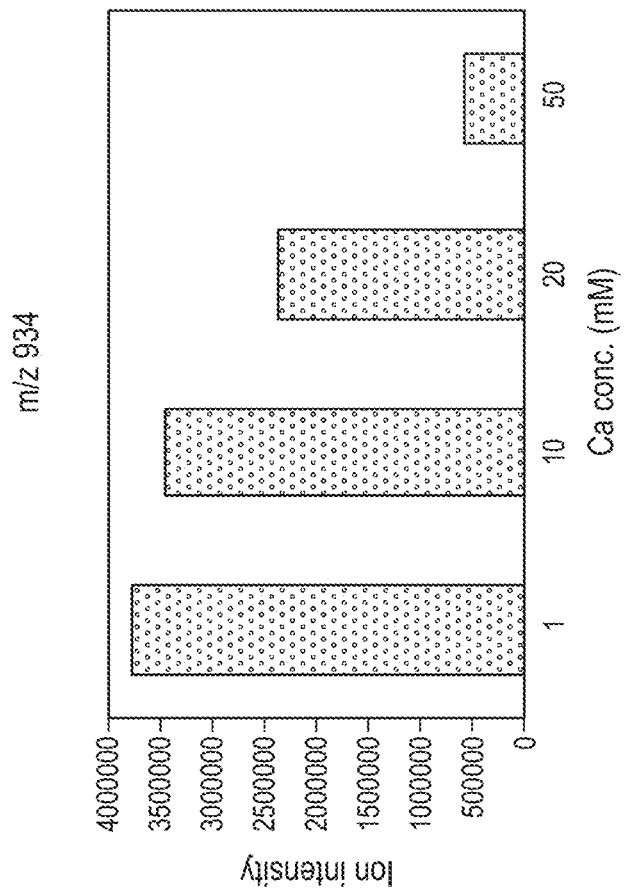
FIGS. 9A and 9B are graphs comparing the effect of $Ca^{2+}$ concentration on digestion efficiency and non-specific binding.
Figure 9A:
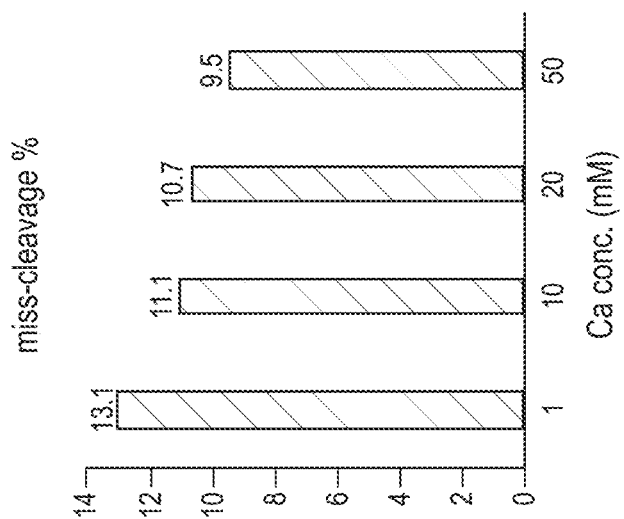

In some examples, buffer composition includes calcium ions ($Ca^{2+}$). The activity of trypsin in its free form could be improved by 1-10 mM $Ca^{2+}$ in solution. With the effect of ionic strength to trypsin, while not being bound by theory, there may be a "sweet-spot" concentration regardless of the inorganic salts. Once immobilized, the enzymatic reaction could be carried out at a much higher temperature. For example, with trypsin, the enzymatic reaction could be carried out at 70° C. In some examples with significantly improved kinetics, the concentration for catalyst $Ca^{2+}$ may need to be re-evaluated. FIGS. 9A and 9B are graphs displaying the effect of $Ca^{2+}$ concentration (1-50 mM) on digestion efficiency and non-specific binding. In one example, the digestion efficiency has increased significantly when the concentration of $Ca^{2+}$ has increased from 1 mM to 50 mM (FIG. 9A). However, $Ca^{2+}$ at 50 mM also showed the most severe loss over a hydrophobic peptide (m/z 934) (FIG. 9B). A balance for enzyme activity and nonspecific binding may be achieved with 10-20 mM $Ca^{2+}$ for most proteins, especially antibody therapeutics whose peptide profiles are very complex.

In some examples, the buffer can have $CaCl_2$ ranging in concentration from about 1 mM to about 50 mM and can be about 100 mM.

Most enzymes exhibit pH preference. For example, trypsin in solution has maximized activity at pH 8.0. The buffers that are used to create such environment are mostly zwitterionic compounds that vary in pKa values, which affect the buffering capacity. With elevated temperature, pKa values usually decrease, which could induce a pH shift of the digestion buffer. For example, the pH of 50 mM Tris solution dropped 0.6 from 25° C. to 75° C. (Table 2, shown below).

Figure 10B:
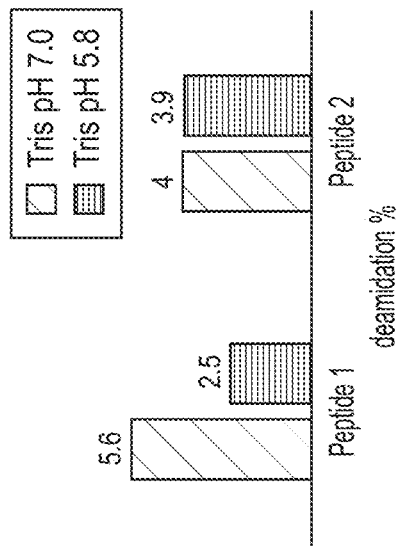
FIGS. 10A and 10B are graphs comparing the effect of pH on digestion efficiency and deamidation percentage (%).
Figure 10A:
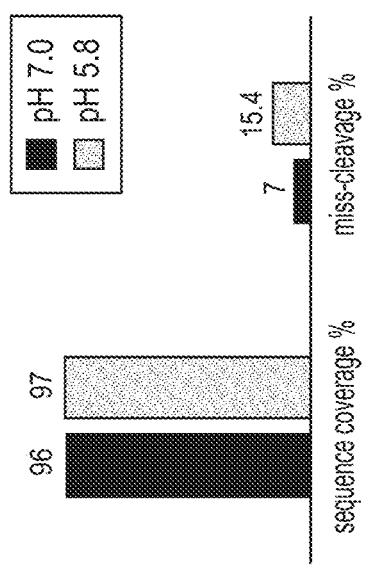

FIGS. 10A and 10B are graphs comparing effect of pH on digestion efficiency and deamidation %. In the example of FIG. 10A, the pH for immobilized trypsin was shifted to 7.0 at 75° C. from 7.6 at 25° C. (FIG. 10A). There are situations where a lower pH is preferred. For example, a heated digestion is known to exert an acceleration of deamidation, but it could be circumvented by adjusting the pH to a slightly lower value (FIG. 10B) or simply shortening the digestion time.

In some examples, a preferred pH for the enzyme can be the same regardless of what temperature the digestion happens. But buffers have different capacity to maintain the same pH across a wide temperature range. In the example of immobilized trypsin, the pH for the buffer is 7.6 at room temperature. At 75° C., the buffer pH has dropped to 7.0. But with the effect of heat, the digestion could occur at a faster speed so even though trypsin was not in a preferred state, the digestion still achieved quality results of digestion in 10 minutes. In some examples, the pH of the digestion buffer is about 7.5.

Figure 11B:
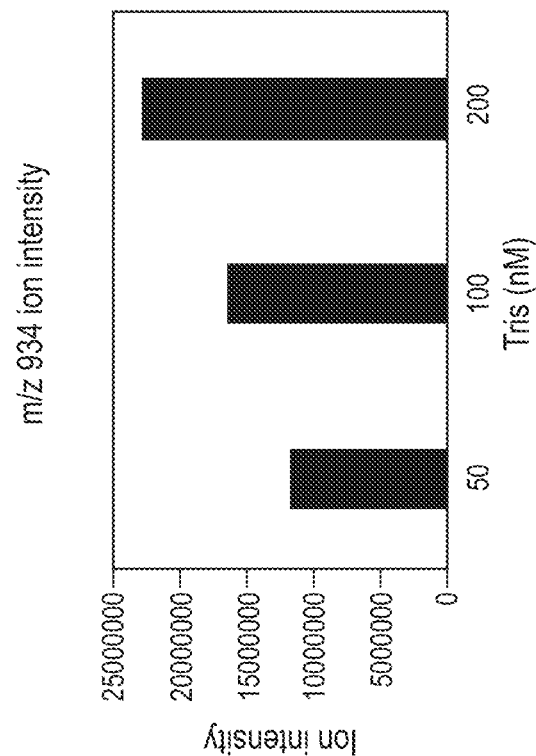
FIGS. 11A and 11B are graphs comparing the effect of Tris concentration on digestion efficiency and non-specific binding.
Figure 11A:
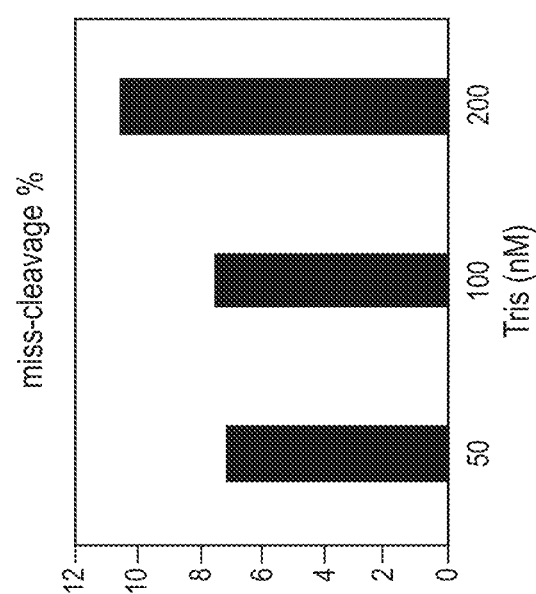

Ionic strength is another buffer composition condition. Each buffer salt at certain concentrations provides ionic strength for an enzymatic reaction to occur. Tris buffer is commonly used for digestion but the concentration of Tris needs to be tailored for the enzyme selected for digestion. FIGS. 11A and 11B are graphs comparing the effect of Tris concentration on digestion efficiency and non-specific binding. In the example of immobilized trypsin, 100 mM of Tris provides best results for balanced digestion efficiency and enhanced peptide recovery (FIG. 11).

In some examples, Tris-HCl of the digestion buffer ranges in concentration from about 50 mM to about 200 mM, e.g., Tris-HCl concentration can be about 100 mM.

Once the immobilized enzyme is chosen for digestion, a thermal mixer is needed to avoid the physical settlement of the resin to ensure an even and efficient heat distribution during the process. However, accelerated aggregation could occur among particles and proteins, for example, denatured proteins may aggregate much faster than in solution with more readily hydrophobic moieties exposed under heat.

Figures 12A, 12B:
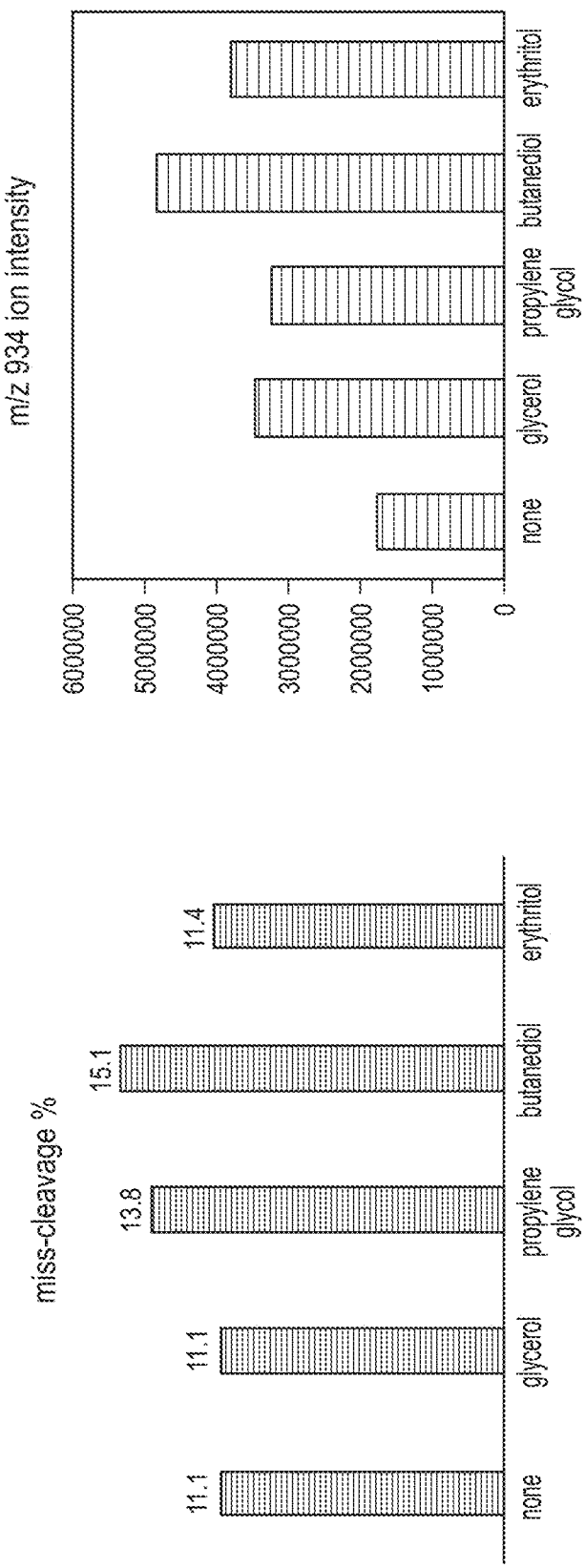
FIGS. 12A and 12B are graphs comparing the effect of polyols on digestion efficiency and non-specific binding.
Figure 12C:
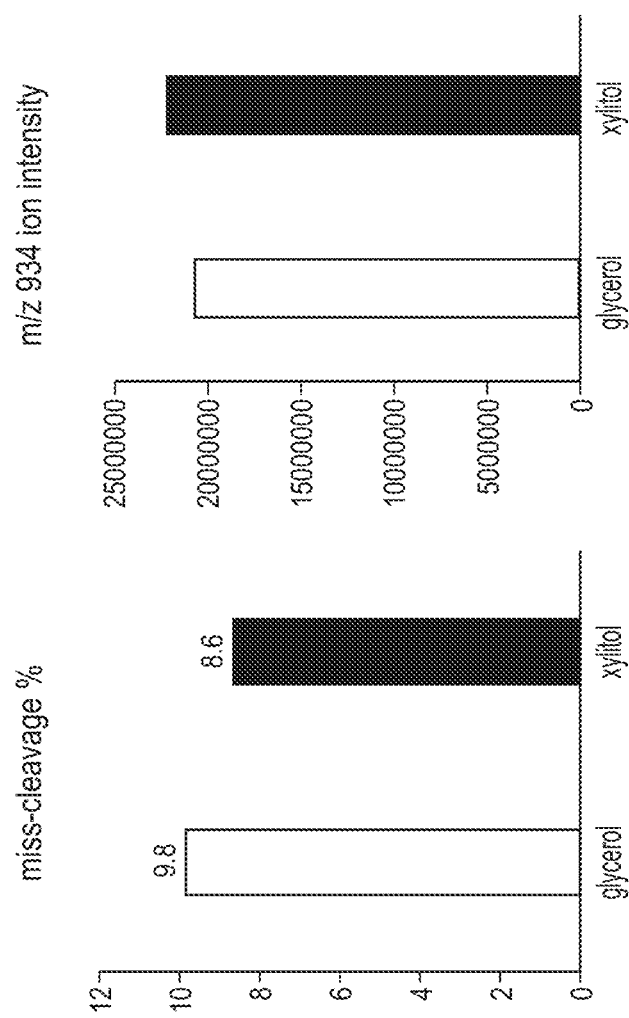
FIG. 12C is a graph displaying the comparison of digestion results using glycerol and xylitol.

Polar additives could play an important role to prevent unfavorable interaction between particles or proteins and nurture an aqueous-like environment. In fact, small polyols including but not limited to glycerol, xylitol, erythritol, propylene glycol, and butanediol could stabilize aggregation at high temperature and salt concentration and provide high recovery % of peptides, given its hydrophilicity properties. FIGS. 12A and 12B are graphs comparing the effect of polyols on digestion efficiency and non-specific binding. FIG. 12C is a graph displaying the comparison of digestion results using glycerol and xylitol. In some examples, the higher the hydrophilicity, the better the digestion efficiency is (FIG. 12).

The buffer may need to be heat stable due to the heat assistance for conducting fast enzyme digestion. In some examples, a polyol enhances heat stability of the buffer solution. Depending on the heat stability requirements among other factors, the polyol and the concentration of that polyol can be varied. Some examples of polyols include xylitol, erythritol, glycerol, propylene glycol, and butanediol. In some examples, the polyol can have a concentration range. For example, xylitol can range in concentration from about 600 mM to about 680 mM. In some examples, the concentration of xylitol can range from about 650 mM to about 660 mM (e.g., xylitol concentration can be about 657 mM).

In the present disclosure, the enzyme activity control included cofactor/stabilizer, ionic strength. In the example of immobilized trypsin, calcium concentration can be tailored to ensure the activity of enzyme. In the example of immobilized trypsin, Tris concentration can also be tailored according to the activity.

In the present disclosure, the non-specific binding control applies to immobilized enzyme. In the example of immobilized trypsin, 5% glycerol and others have effect to alleviate hydrophobic peptide adsorption onto the surface of resin. In the example of immobilized trypsin, calcium and Tris concentration can be tailored for minimal nonspecific binding.

Figure 13:
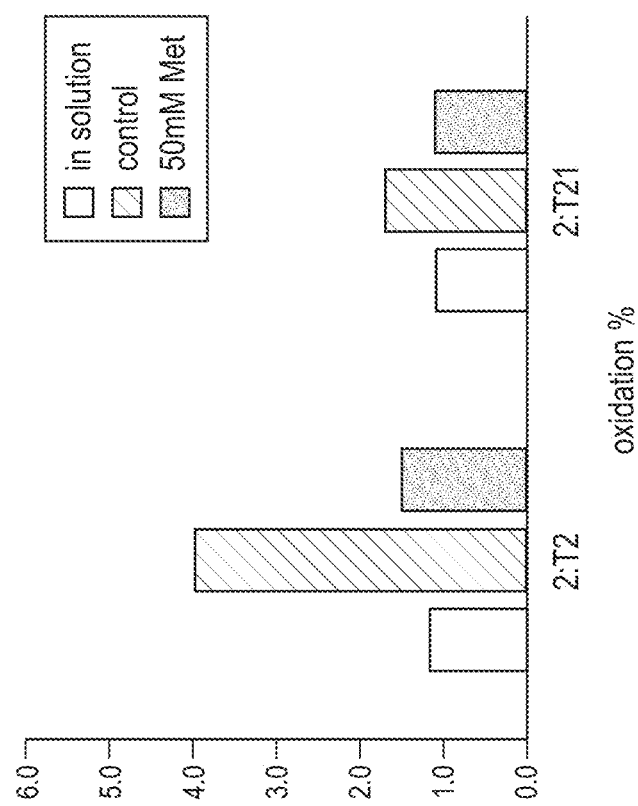
FIG. 13 is a graph displaying the effect of methionine on preventing artificial oxidation.
Figure 14:
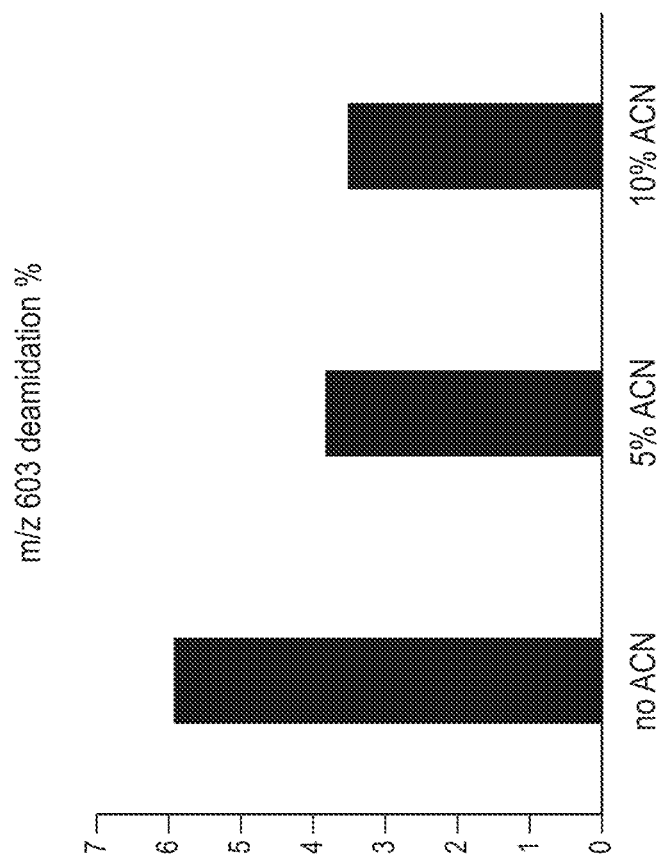
FIG. 14 is a graph displaying the effect of acetonitrile on reducing artificial deamidation.

As is always a concern for process-induced modification associated with elevated temperature, there are additives that could circumvent this problematic effect. FIG. 13 is a graph displaying the effect of methionine on preventing artificial oxidation. For example, the addition of sufficient amount of oxidation scavengers, such as methionine, could sufficiently reduce artificial oxidation (FIG. 13). In the case of deamidation, the addition of organic solvent, for example, 10% acetonitrile could modulate the dielectric strength and alleviate method-induced deamidation (FIG. 14).

A kit can include a digestion buffer to support enzymatic activity at an elevated temperature and minimize heat-induced modifications on the protein. In some examples, less than a 1% relative conversion rate for a methionine containing peptide is to be converted to an oxidized variant. In some examples, less than a 5% relative conversion rate for an asparagine residue is to be deamidated to an isoaspartic acid or aspartic acid, preferably less than 2%, during the course of the kit procedure. In some examples, within 10 minutes of heated digestion at pH 7.5, there is no more than 1% of artificial oxidation on methionine and no more than 5% of deamidation. 20.

Low mM concentration of methionine (up to 300 mM tested in Example 14) can function as oxidation scavenger to prevent method-induced oxidation on peptides, however at a higher concentration (300 mM), methionine can negatively affect peptide recovery. In some examples, a buffer having methionine can range in concentration from about 100 mM to about 300 mM. In some examples, 200 mM of methionine is adopted in the buffer to prevent artificial oxidation and ensure sufficient recovery of hydrophobic peptide Oxidation scavengers like methionine can be added to digestion buffer. In one example of immobilized trypsin, 50 mM of methionine was able to eliminate heat-induced modification compared to in-solution digestion. In some examples, an oxidation scavenger maintains a ratio with another component of the digestion buffer. For example, the digestion buffer can include arginine and an oxidation scavenger, wherein the ratio of arginine to the oxidation scavenger ranges from about 1:15 to about 1:30. In some examples, the range can be about 1:20. That is, stated another way, a concentration of about 10 mM arginine to about a concentration of 200 mM methionine.

Deamidation is a pH-driven process. Lowering the pH or adjusting the composition of buffer can prevent head-induced deamidation. In the examples of immobilized trypsin, 10% of acetonitrile can significantly reduce artificial deamidation.

To achieve complete digestion, time-dependent studies are needed for each enzyme with the protein digested. In the example of immobilized trypsin, the digestion can be completed in 1-10 minutes.

Figure 15:
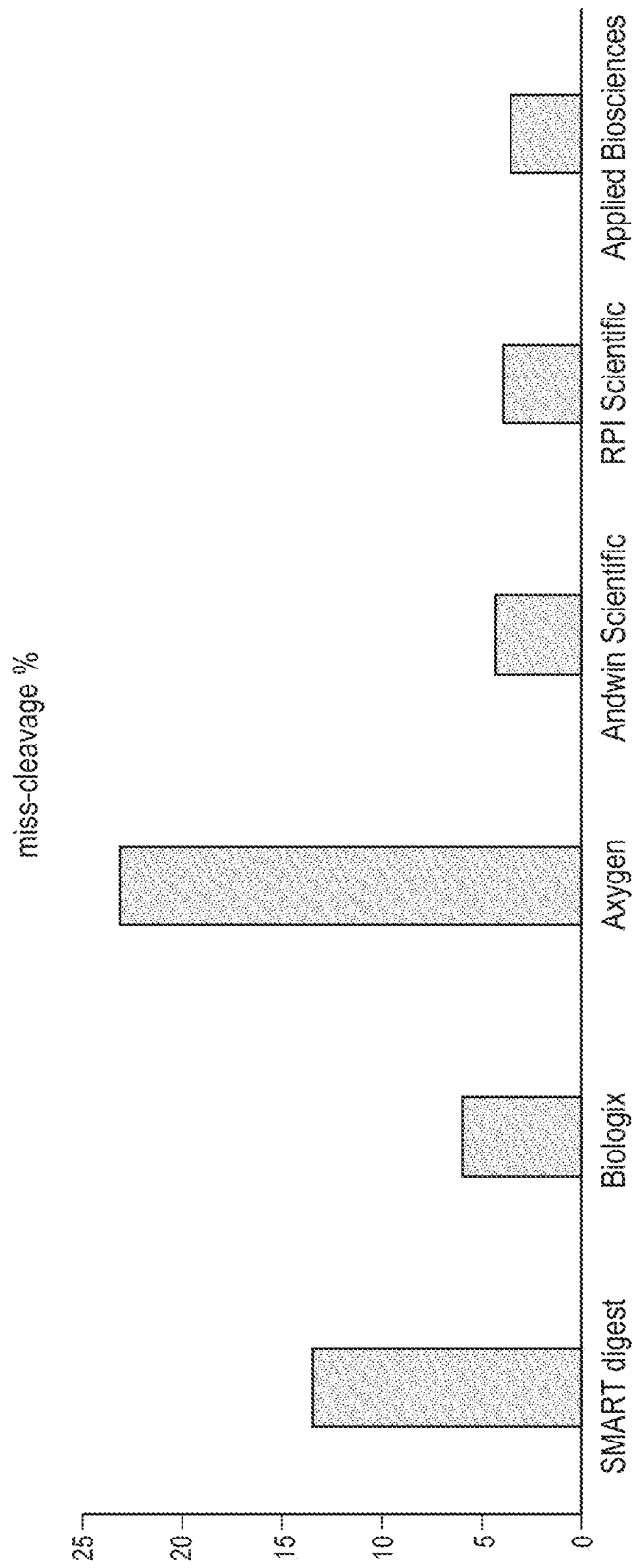
FIG. 15 is a graph displaying digestion efficiency comparison among examples.
Figure 16:
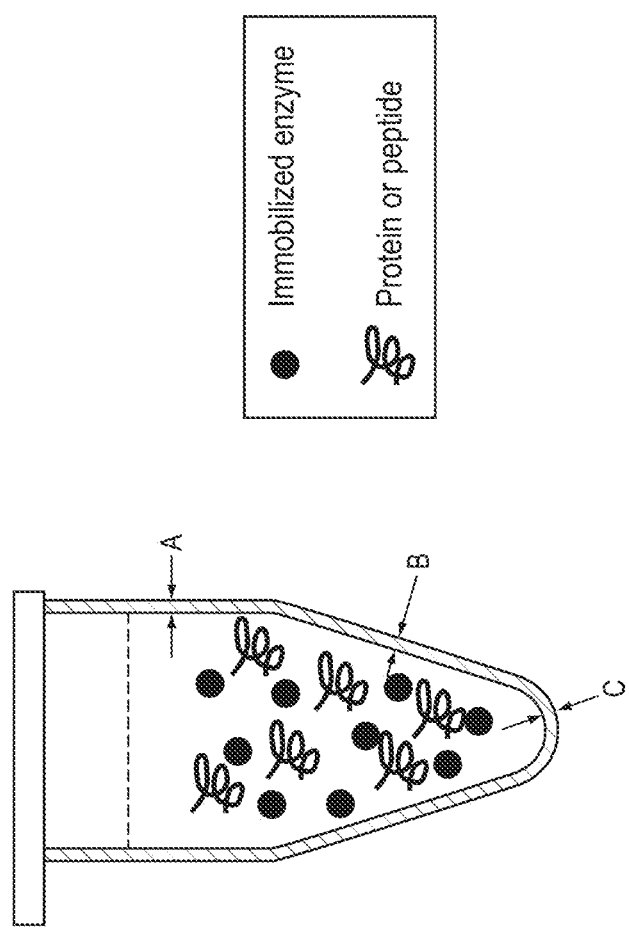
FIG. 16 displays a typical reaction set-up in a 200 µL PCR tube.
Figure 17:
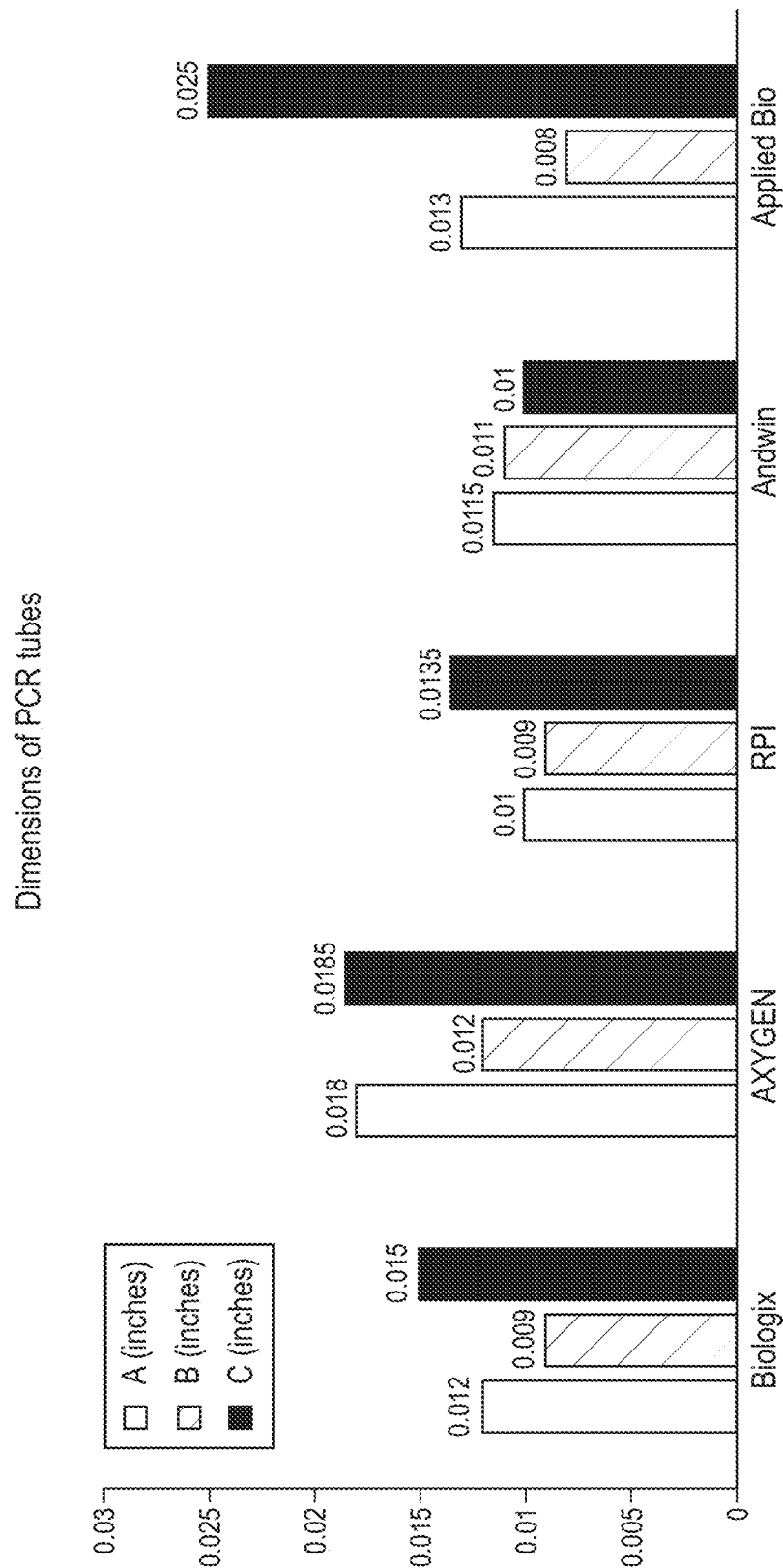
FIG. 17 displays dimensions of PCR tubes from the tubes used in FIG. 15.

According to the present disclosure, the heat-assisted digestion could be completed in minutes and thus it is compatible in both dispersive and an online column format. For reactions in the vials, with a 200 µL volume of reaction, the ramp up time can be problematic since it takes minutes for the mixture to reach the set temperature. Depending on the tube and thermos-mixer that are used, the ramp up time can vary. In order to achieve high reproducibility for this process, robust heat transfer efficiency is important. Commercially available PCR tubes mostly made from polypropylene have shown varied wall thickness. FIG. 15 is a graph displaying digestion efficiency comparison among examples. Specifically, FIG. 15 is a graph displaying digestion efficiency comparison among SMART Digest™ (a protein digestion kit available from Thermo Fischer Scientific, Waltham, MA) and immobilized prototypes (i.e., silica-based solid supports with coating of the present technology) in PCR tubes by 5 different vendors. FIG. 16 displays a typical reaction set-up in a 200 µL PCR tube. Cross sections A, B, and C correspond to the cross section dimensions of FIG. 17. FIG. 17 displays dimensions of PCR tubes from the tubes used in FIG. 15. The thickness at the bottom of the tube (dimension C) seems to have the least impact on digestion. For example, AXYGEN has the thickest A and B dimensions, which possibly contributed to poor heat transfer that resulted in the worst digestion performance as shown in FIG. 15.

The variation in wall thickness can affect the digestion performance significantly (FIG. 15). Moreover, the material of the tube needs to be considered. For example, polypropylene or glass can cause non-specific binding issues. To address these issues, use of a surface coated/treated polypropylene or glass container, vial, or well plate that creates non-binding surfaces, such as QuanRecovery Vials and Plates (available from Water Technologies Corporation, Milford, MA) can be utilized. The non-specific binding issues can be addressed by introducing plasma treatment. Blocking reagents, even though useful at times, could cause severe noise or peptide loss for downstream analysis in situations of bovine serum albumin, surfactants, organic solvents and detergents. 200 µL PCR tubes could be easily transitioned to a PCR plate if more samples need to be processed at one time, or even to a 384 well plates.

The present disclosure also includes steps after digestion. For modified enzyme, quenching is required to terminate the reaction. The trypsin digestion can be stopped by freezing or by lowering the pH of the reaction below pH 4 by adding formic, acetic, or trifluoroacetic acid.

Immobilized enzyme, if in a dispersive format, can require removal of the solid support either by centrifugation, filtration or magnetic beads removal. Filter membranes or devices used can be selected to have minimal non-specific binding of the peptides or other analytes of interest.

Automating systems that utilize a plate format for digestion with liquid handling features, can include denaturation, reduction, alkylation, desalting device, and digestion completed on a heater. If immobilized enzyme is used, enzymes can be removed through positive pressure manifold or vacuum-assisted filtration. If modified enzyme in-solution is used, the reaction can be quenched for downstream analysis.

Automating systems can include a flow through mode of digestion, where protein is digested while traveling through a column, a chip or any surface, with or without pretreatment.

The removal of resin from the reaction mixture can be done in different ways, including centrifugation and filtration. The filtration process may introduce sample loss since membranes made from cellulose acetate or polyvinylidene fluoride (PVDF) are known to absorb peptides. Inert materials or modified membranes should be considered for maximum recovery.

Figures 3A, 3B:
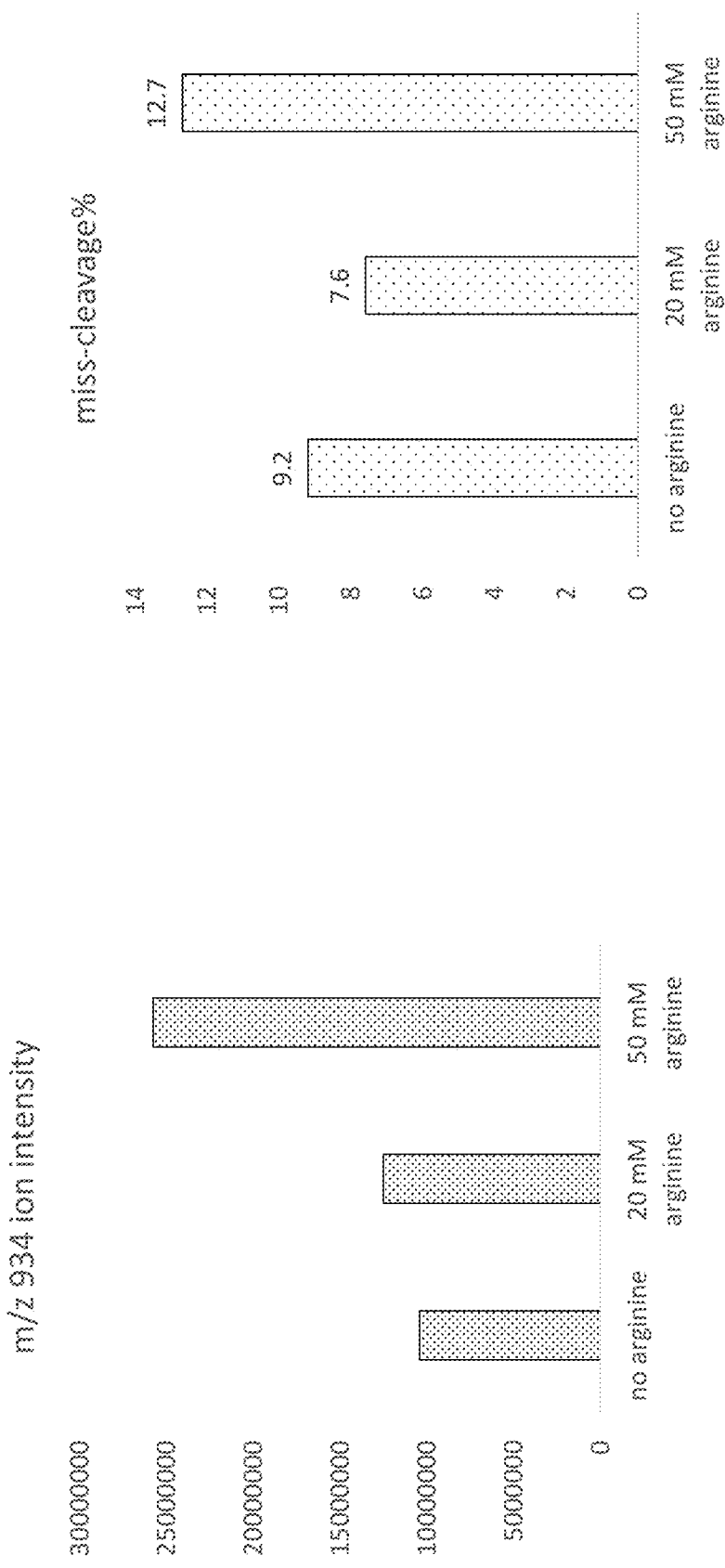
FIG. 3A is a graph illustrating the effect on hydrophobic peptide recovery of adding arginine to a digestion buffer.
FIG. 3B is a graph illustrating the effect on digestion efficiency of adding arginine to the digestion buffer.

In some examples, the loss of sample could be significantly reduced with addition of low concentrations (~5-100 mM) of arginine, di-methyl-arginine, guanidine, or other derivatives that present chaotropic properties to the digestion buffer. These chaotrope reagents at relatively low concentration could reduce the nonspecific binding during filtration while not affecting the enzyme reaction in a significant way. Alternatively, they could be added during the filtration step to either pre-treat the filter or simultaneously filtered with the digest to minimize nonspecific binding. These measures may ensure decent hydrophobic peptide recovery. For example, FIG. 3A and FIG. 3B illustrate the effect on hydrophobic peptide recovery (FIG. 3A) and digestion efficiency (FIG. 3B) by introducing low concentrations (20 mM and 50 mM) additions of arginine. FIG. 3C provides the effect on hydrophobic peptide recovery by introducing 5 mM and 20 mM of di-methyl arginine. And FIG. 3D provides the effect on digestion efficiency by introducing 5 mM and 20 mM of di-methyl arginine.

Low mM concentration of arginine (up to 20 mM tested in Example 13) can significantly improve the recovery of analytes of interest, e.g., a hydrophobic peptide, but the addition of arginine can also introduce higher deamidation percentage (%) that is not desirable for monitoring such attributes. In some examples, 10 mM of arginine can be adopted in the buffer to provide sufficient recovery of analytes of interest, e.g., peptides.

Based on the examples provided herein, an example buffer solution can include 100 mM Tris-HCl, 10 mM $CaCl_2$, 657 mM xylitol, 10 mM arginine, 200 mM methionine with a digestion buffer of pH 7.5.

In some examples, the technology provides a method of processing a sample including protein. The method can include the following steps: adding the sample to an apparatus containing a buffer and a solid support surface comprising a surface coating, wherein the surface coating immobilizes enzymes and affinity ligands while reducing undesired interactions between the sample and the solid support surface; immobilizing enzymes on the surface coating for digesting the protein in the sample; immobilizing affinity ligands on the surface coating for target capturing a portion of the sample; digesting the protein in the sample with the immobilized enzymes on the surface coating; target capturing the portion of the sample with the immobilized affinity ligands on the surface coating; and heating the sample to activate digestion of the protein.

The step of target capturing the portion of the sample can occur before, during, or after the step of digesting the protein in the sample. In some embodiments, the step of target capturing a portion of the sample occurs before, during, and/or after the step of digesting the protein (e.g., 2 of the 3, or all 3 of the indicated timeframes of digestion). The method can also include tuning a reaction condition to determine whether the step of target capturing the portion of the sample occurs before, during, or after the step of digesting the protein in the sample.

The reaction condition can include a buffer composition, reaction temperature, or reaction pH. The solid support surface can be a particle. In some examples, the enzymes and the affinity ligands are immobilized on the same particle. Heating the sample to activate purification or digestion of the protein in the sample can include digesting the protein in the sample with the immobilized enzymes at an elevated temperature. There can be more than one buffer when processing the sample. For example, there can be a target capturing elution buffer and a digesting buffer.

The above method can utilize any type of affinity ligand. Examples of affinity ligands that can be utilized include, but are not limited to: immoglobin-binding protein such as protein A, G, L or a mixture thereof. The affinity ligand can also be antigen binding such as an antibody, nanobody, or a mixture thereof. The affinity ligand can also be an aptamers.

The affinity ligand can be immobilized on a solid support with a coating covering the solid support surface. The coating can provide a surface coverage of at least 5 μmoles/m² and reduce undesired interactions between protein sample and the solid support surface and has functionality to covalently bind the affinity ligand. The solid support on which the affinity ligand is immobilized can be a nonporous or a porous or magnetic, in the form of a membrane, particle, a monolith, a surface of a device, surface of a microchip. The immobilized affinity ligand is packed into a device. The device is a plate well, tip of a pipette, a channel on a microchip or a tube with one end or both end frits.

It will be understood by those skilled in the art that various changes in form and details may be made therein without departing from the scope of the technology of the present disclosure. For example, alternative modifications include:

Format factor of the reaction mixture (50, 100, 200, 500, 1000 μL)

Immobilized resin packed in columns, in tips, in filtration plates

Enzymes besides trypsin (chymotrypsin, pepsin, protease K, lysC, IdeS, Glu-C, Arg-C, Asp N, papain pronase and PNGase F and a combination)

Enzyme modified with different hydrophilic cross-linkers, modifiers;

For some proteins, not every step of the digestion workflow needs to be performed. Proteins without disulfide bonds do not need to be reduced and alkylated and oftentimes heating itself could facilitate the denaturation.

Alternative uses (e.g., for biopharmaceutical applications) include:
Bioanalysis sample preparation
Released glycan sample preparation
Subunit analysis sample preparation
Proteomics sample preparation Results Example 1. Thermal Stability of Immobilized Enzyme Through NanoDSC NanoDSC is routinely used to study the thermodynamics of proteins or polymers. In a NanoDSC experiment, the protein sample in a buffer solution was scanned at a certain heat rate (° C./min), during which the peptide bonds and interactions are disrupted. The unfolding process continues until the protein are fully denatured. The temperature at the midpoint of the unfolding process dictates when half the molecules are unfolded, which indicates the thermal stability of the protein. In this example we used trypsin to investigate the benefit of immobilization. The NanoDSC run was set at 1° C./min scanning from 10° C. to 100° C. for all samples. Each sample contained ~1 mg/mL trypsin and ~330 μL was used for was scanned twice, with the second scan serving as the reference scan to account for changes that are induced not by trypsin denaturation. As shown in FIG. 1, when trypsin is immobilized on to a solid support, $T_m$ has shifted from ~45° C. to 80° C. There was also significant improvement by the silica-based prototype on $T_m$, with at least 5° C. increase in comparison with the commercial product Smart Digest™.

Example 2. Thermal Stability of Immobilized Trypsin with Modification Through NanoDSC Preferably, two hydrophilic crosslinkers with a preferred length were selected. As shown in FIG. 2, the $T_m$ of crosslinked trypsin has increased 5° C. in comparison to unmodified trypsin. Point modification that targets a particular amino acid also presented some improvement on $T_m$ though not as significant, shown in FIG. 2.

Example 3. Nonspecific Binding Test on Surface Chemistry of Immobilization Support 10 μg of NIST mAb standard digest (Waters) was mixed with 10 μL of resin and diluted to 200 μL with digestion buffer that contains 50 mM Tris, 250 mM $CaCl_2$ and 5% glycerol. The mixture was incubated at 75° C. for 5 min on a shaker Eppendorf ThermoMixer® C (available from Eppendorf, Hamburg, Germany) at 1400 rpm and then centrifuged 3,000 g for 1 min before 100 μL of supernatant was submitted for LC-MS analysis.

The nonspecific binding effect of two different surface chemistry was evaluated by mixing a NIST mAb digest with a similar pore size (450~500 Å). After 5 min incubation the peptides are collected for analysis. It's shown here that among the selected hydrophobic peptides, the modified PS-DVB had the worst recovery of all. Similarly, the nonspecific binding effect was tested among different hydrophilic coating with the same amount of trypsin immobilized. Shown in FIG. 4, Smart Digest™ showed worse recovery for all the peptides tested. However, this fundamental test reflects only on the nonspecific binding effect after the peptide is digested from the protein.

TABLE 1

Parameters for LC-MS analysis on BioAccord

ACQUITY I-Class PLUS

Detection: ACUITY TUV
Column: ACUITY UPLC BEH C18 column (p/n 186003555)
Column temp.: 65° C.
Sample temp.: 6° C.
Injection volume: 10 μL
Flow rate: 0.25 mL/min
Mobile phase A: 0.1% formic acid in H2O
Mobile phase B: 0.1% formic acid in acetonitrile
Gradient: 1% B over 5 min, 1%-40% B over 65 min,
15% B over 2 min and 1% B for 14 min

ACQUITY RDa Detector

MS system: ACQUITY RDa Detector
Ionization mode: ESI positive
Acquisition range: m/z 50-2000
Capillary voltage: 1.2 kV
Collision energy: 60-120 V
Cone voltage: 30 V
Desolvation energy: 350° C.
Intelligent data capture: on

Example 4. Quantification of Released Trypsin

10 μL of resin was diluted to 200 L with digestion buffer that contains 50 mM Tris, 250 mM $CaCl_2$ and 5% glycerol. The mixture was incubated at 75° C. for 30 min and 60 min on a shaker (Eppendorf thermo mixer C) at 1400 rpm and then centrifuged 3,000 g for 1 min before 100 μL of supernatant was submitted for Fluorescence analysis (Excitation: 280 nm, Emission: 370 nm). Free trypsin dissolved in the digestion buffer with a concentration ranging from 0.004 mg/mL to 0.4 mg/mL was used for generating calibration curve.

The released trypsin was quantified after 30- and 60-min incubation at 70° C. Shown in FIG. 5, a ~20% loss of immobilized trypsin was observed on Smart Digest™ after 30 min incubation while the other prototype (i.e., a silica-based solid support with coating of the present technology) showed less than 10%.

Example 5. NIST mAb Digestion with Immobilized Enzyme

Approximately 50 μg of NIST mAb was denatured and reduced in 8 M guanidine buffer with 5 mM DTT for one hour followed with alkylation for 30 min in the dark with 15 mM IAM. The alkylated protein then was desalted using NAP-5 columns (GE Healthcare) and mixed with 15 μL immobilized enzyme. The digestion was conducted at 70° C. for 10 min on a shaker before 100 μL of supernatant was submitted for LC-MS analysis.

Shown in FIG. 6, NIST mAb was used as a model protein to be digested by immobilized trypsin. The peptide map generated through a standard LC-MS assay exhibited similar overall profiles as in solution digestion, however, Smart Digest™ suffered more severe incomplete digestion, with more than 20% miss-cleavage while a better prototype showed only ~8% (FIGS. 7 & 8). Incomplete digestion could be a result of unfavorable surface chemistry of the immobilization support that induces nonspecific binding and interaction, and it could also be related to deconjugation of trypsin as discussed in Examples 3 & 4. The tested prototype utilized a hydrophilic coating that could be tuned in "thickness" to maximize digestion efficiency. Shown in FIG. 7, best digestion efficiency was achieved with a preferred coating of the modifier labeled as modified prototype 3.

Example 6. Effect of Temperature on Digestion Efficiency

Samples were digested at 60, 70, 80° C. according to Example 5 as shown in FIGS. 8A, 8B, and 8C.

Example 7. Effect of $Ca^{2+}$ on Digestion Efficiency and Nonspecific Binding 1-50 mM of $Ca^{2+}$ was evaluated for its impact on digestion according to Example 5 as shown in FIGS. 9A and 9B.

Example 8. Effect of pH on Digestion Efficiency and Deamidation

Samples were digested at pH 7.6 and 6.6 according to Example 5, shown below in Table 2.

TABLE 2 pH of buffer measured at different temperature

| Temperature | the pH of 50 mM Tris solution | the pH for immobilized trypsin |
|---|---|---|
| 25° C. | 7.6 | 6.6 |
| 70° C. | 7.0 | 5.8 |

Example 9. Effect of Additives on Digestion Efficiency

5% of polyols were added to digestion buffer and samples were digestion according to Example 5. 50 mM methionine was evaluated for its effect on preventing artificial oxidation. 5%, 10% acetonitrile were added to digestion buffer to evaluate its effect on reducing artificial deamidation as shown in FIG. 14.

Example 10. PCR Tubes Screening

Samples were digested in 5 different PCR tubes that were from Biologix, Axygen, Andwin Scientific, RPI Scientific and Applied Biosciences according to Example 5 (See FIGS. 15 and 17).

Example 11. Tris Concentration Optimization 50, 100, and 200 mM Tris was used as the digestion buffer and protein samples were digested at 70° C. according to Example 5 as shown in FIGS. 10A and 10B.

Example 12. The Effect of Arginine and Dimethyl-Arginine on Hydrophobic Peptide Recovery 5, 20 mM of dimethyl-arginine and 20, 50 mM of arginine were added to the digestion buffer and protein samples were digested at 70° C. according to Example 5 as shown in FIGS. 3A and 3B. All protein digests were filtered by a PVDF-membrane filter with a positive pressure manifold.

Example 13. The Effect of Arginine on Hydrophobic Peptide Recovery

Figure 19B:
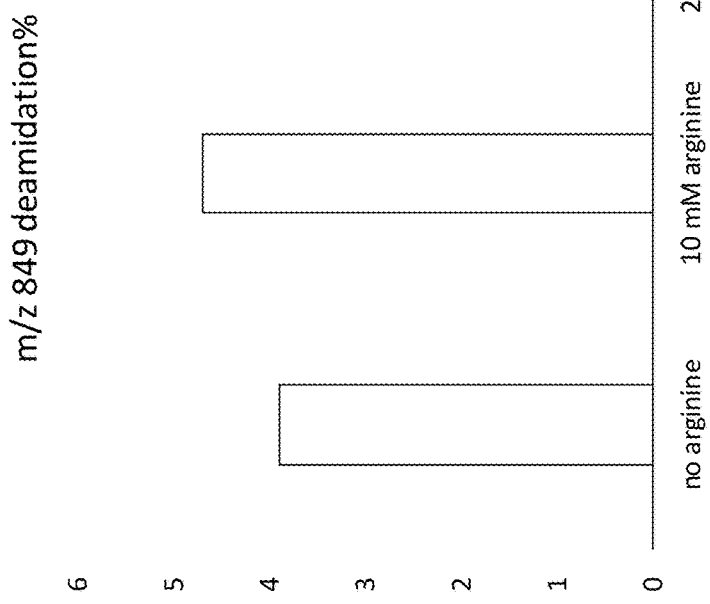
FIG. 19A and FIG. 19B are graphs relating to arginine in accordance with the present disclosure.
Figure 19A:
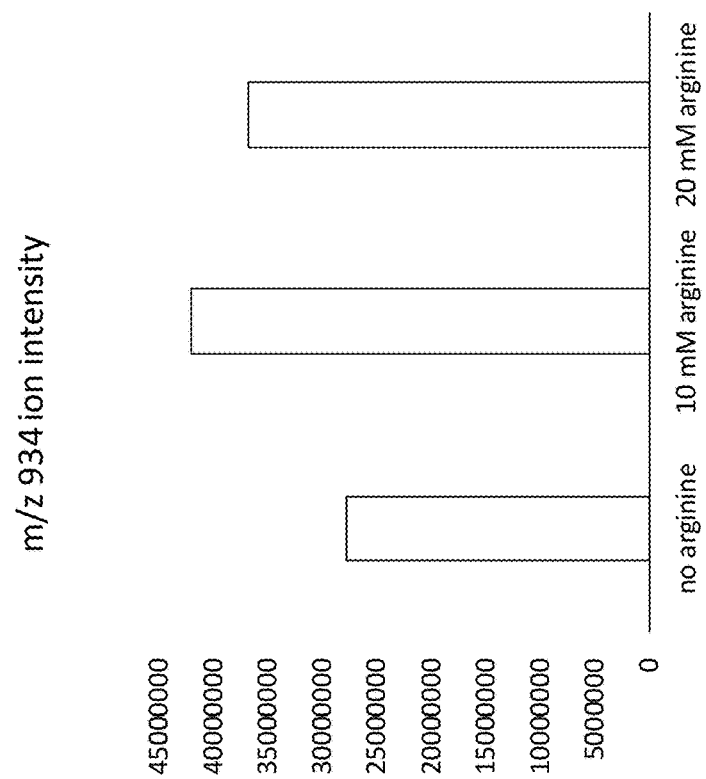

FIG. 19A and FIG. 19B are graphs relating to arginine in accordance with the present disclosure. FIG. 19A is a graph illustrating the effect on hydrophobic peptide recovery of adding arginine to a digestion buffer. FIG. 19B is a graph illustrating the effect on method induced deamidation % of adding arginine to the digestion buffer. FIG. 19B displays the effect of arginine in digestion buffer on deamidation percentage (%) observed after digestion. Other components of the buffer include 10 mM $CaCl_2$, 657 mM xylitol, 50 mM Methionine.

Low mM concentration of arginine (up to 20 mM tested in Example 13) can significantly improve the recovery of hydrophobic peptide, but the addition of arginine can also introduce higher deamidation percentage (%) that may not be desirable for monitoring such attributes. In this example, limiting the arginine in the buffer to a concentration of about 10 mM provides sufficient recovery of peptides without increasing deleterious properties.

Example 14. The Effect of Methionine on Hydrophobic Peptide Recovery

Figures 20A, 20B:
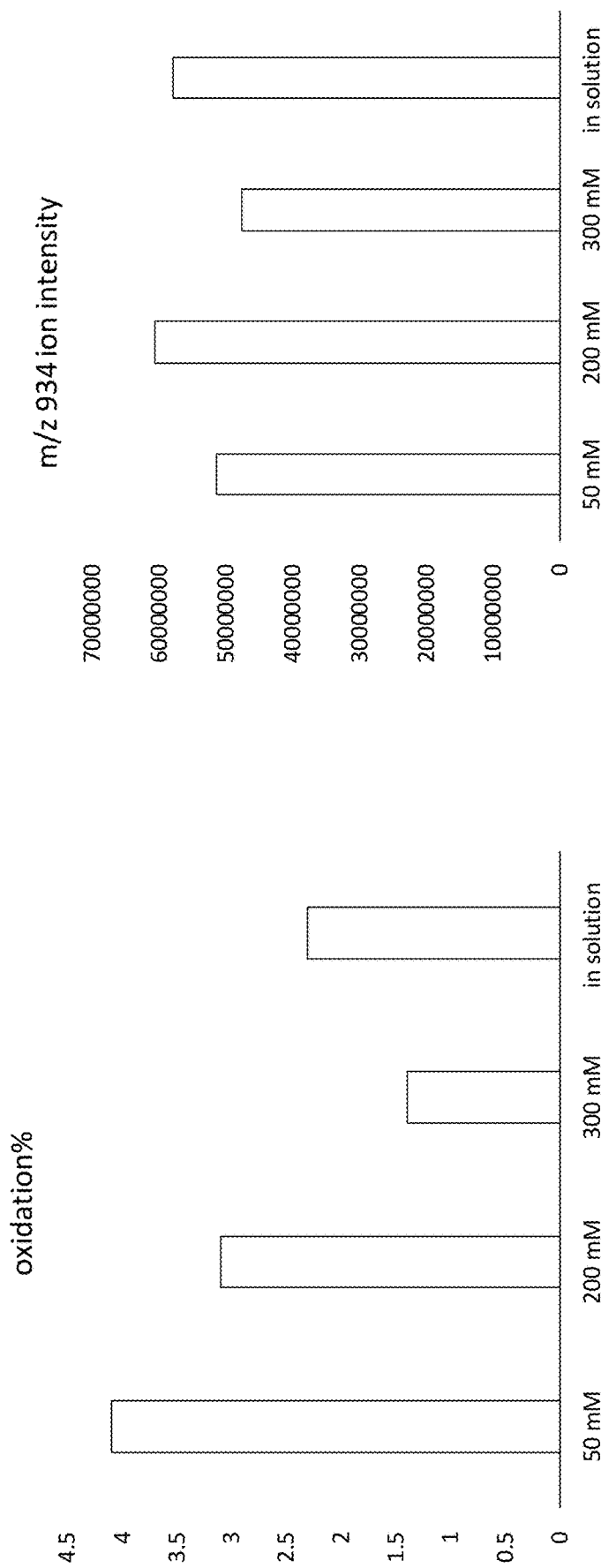
FIG. 20A and FIG. 20B are graphs relating to methionine in accordance with the present disclosure.

FIG. 20A and FIG. 20B are graphs relating to methionine in accordance with the present disclosure. FIG. 20A is a graph illustrating the effect on oxidation percentage (%) of adding methionine to a digestion buffer. FIG. 20B is a graph illustrating the effect on peptide recovery of adding methionine to the digestion buffer. Other components of the buffer include 10 mM $CaCl_2$, 657 mM xylitol, 10 mM arginine.

Low mM concentration of methionine (up to 300 mM tested in Example 14) could function as oxidation scavenger to prevent method-induced oxidation on peptides, however at a higher concentration (300 mM), it may start to negatively affect peptide recovery. As a result, 200 mM of methionine was adopted in the buffer to prevent artificial oxidation and ensure sufficient recovery of hydrophobic peptides.

While this disclosure has been particularly shown and described with reference to example embodiments thereof, it will be understood by those skilled in the art that various changes in form and details may be made therein without departing from the scope of the technology encompassed by the claims.

What is claimed is:

1. A kit for protein sample preparation, the kit comprising:
a solid support surface with a polymer coating covering the solid support surface, wherein the polymer coating comprises a first coating portion with functionality for bioconjugation and a second coating portion comprising a diol obtained from hydrolysis of an epoxide containing silane selected from the group consisting of a 3-glycidopropyl trifunctional silane and a 2-(3,4-epoxycyclohexyl) ethyl trifunctional silane, wherein the second coating portion renders the surface hydrophilic and reduces non-specific binding between a protein sample and the solid support surface, wherein the polymer coating is present at a total surface coverage of at least 5 µmoles/m$^2$;
a container containing a buffer solution; and
a vessel for containing the solid support surface and the buffer solution, wherein the buffer solution comprises:
5% to 10% acetonitrile;
from about 10 mM to about 20 mM arginine;
from about 100 mM to about 300 mM methionine;
from about 50 mM to about 200 mM Tris-HCl;
from about 10 mM to about 20 mM $CaCl_2$); and
a polyol selected from the group consisting of xylitol, erythritol, glycerol, propylene glycol, and butanediol.

2. The kit of claim 1, wherein the polyol is xylitol and the concentration of xylitol ranges from about 600 mM to about 680 mM.

3. The kit of claim 1, wherein the arginine concentration is about 10 mM.

4. The kit of claim 1, wherein the methionine concentration is about 200 mM.

5. The kit of claim 1, further comprising a heat source.

* * * * *